(12) United States Patent
Sims et al.

(10) Patent No.: US 7,659,375 B2
(45) Date of Patent: Feb. 9, 2010

(54) HUMAN IL-1 EPSILON DNA AND POLYPEPTIDES

(75) Inventors: John E Sims, Seattle, WA (US); Dirk E Smith, Bainbridge Island, WA (US)

(73) Assignee: Immunex Corporation, Thousand Oaks, CA (US)

( * ) Notice: Subject to any disclaimer, the term of this patent is extended or adjusted under 35 U.S.C. 154(b) by 388 days.

(21) Appl. No.: 11/821,853

(22) Filed: Jun. 25, 2007

(65) Prior Publication Data

US 2008/0108796 A1    May 8, 2008

Related U.S. Application Data

(62) Division of application No. 10/986,744, filed on Nov. 12, 2004, now Pat. No. 7,250,276, which is a division of application No. 09/763,498, filed as application No. PCT/US99/18771 on Aug. 20, 1999, now Pat. No. 6,949,359.

(60) Provisional application No. 60/097,413, filed on Aug. 21, 1998, provisional application No. 60/098,595, filed on Aug. 31, 1998, provisional application No. 60/099,974, filed on Sep. 11, 1998.

(51) Int. Cl.
*C07K 16/00* (2006.01)
*C07K 14/52* (2006.01)

(52) U.S. Cl. .............. 530/387.1; 530/387.9; 530/388.1; 530/388.23; 530/389.1; 530/389.2; 530/351

(58) Field of Classification Search ........................ None
See application file for complete search history.

(56) References Cited

U.S. PATENT DOCUMENTS

| | | | |
|---|---|---|---|
| 4,376,110 A | 3/1983 | David et al. | |
| 4,411,993 A | 10/1983 | Gillis | |
| 4,486,530 A | 12/1984 | David et al. | |
| 4,518,584 A | 5/1985 | Mark et al. | |
| 4,543,439 A | 9/1985 | Frackelton, Jr. et al. | |
| RE32,011 E | 10/1985 | Zimmerman et al. | |
| 4,546,082 A | 10/1985 | Kurjan et al. | |
| 4,737,462 A | 4/1988 | Mark et al. | |
| 4,902,614 A | 2/1990 | Wakabayashi et al. | |
| 4,965,195 A | 10/1990 | Namen et al. | |
| 4,968,607 A | 11/1990 | Dower et al. | |
| 5,011,912 A | 4/1991 | Hopp et al. | |
| 5,071,972 A | 12/1991 | Larsen | |
| 5,151,412 A | 9/1992 | Brown | |
| 5,248,599 A | 9/1993 | Sakiyama et al. | |
| 5,350,683 A | 9/1994 | Sims et al. | |
| 5,426,048 A | 6/1995 | Gearing | |
| 5,449,758 A | 9/1995 | Hartley | |
| 5,783,672 A | 7/1998 | Mosley et al. | |

6,197,551 B1    3/2001    Busfield

FOREIGN PATENT DOCUMENTS

| | | |
|---|---|---|
| EP | A-36776 | 9/1981 |
| EP | A-73657 | 3/1983 |
| EP | A-0367566 | 5/1990 |
| EP | 460846 | 12/1991 |
| EP | 324274 | 11/1993 |
| EP | 367566 | 5/1997 |
| EP | 0 855 404 A | 7/1998 |
| WO | WO 90/10448 | 9/1990 |
| WO | WO 90/13641 | 11/1990 |
| WO | WO 91/04753 | 4/1991 |
| WO | WO 91/06629 | 5/1991 |
| WO | WO 98/47921 | 10/1998 |
| WO | WO 99/35268 | 7/1999 |
| WO | WO 99/37662 | 7/1999 |
| WO | WO 00/11174 | 3/2000 |

OTHER PUBLICATIONS

U.S. Appl. No. 07/701,415, filed May 16, 1991, Sims et al.
Ashkenazi, A., et al., "Protection against endotoxic shock by a tumor necrosis factor receptor immunoadhesin," Proc. Natl. Acad. Sci. USA, 1991, 88:10535-10539.
Ashwell, Jonathan D., "The many paths to p38 mitogen-activated protein kinase activation in the immune system," Nature Reviews, 2006, 6:532-540.
Ausubel, et al., Ed. Board, Current Protocols in Molecular Biology, vol. 2, (John Wiley & Sons, Inc., (1996)), 10.3.1-10.3.12.
Bauer, et al., "A genetic enrichment for mutations constructed by oligoeoxynucleotide-directed mutagenesis," Gene, 1985, 37:73-81.
Bazan, et al., "A newly defined interleukin-1?" Nature, Feb. 15, 1996, 379:591.
Beier, et al., "Characterization of a regulatory region upstream of the ADR2 locus of S. cerevisiae," Nature, 1982, 300:23-30.
Berenson, et al., "Autologous Hematopoietic Reconstitution of Lethally Irradiated Dogs using IA-Positive Bone Marrow Cells," J. of Cellular Biochemistry, 1986, Suppl 10D:239.
Bitter, et al., "Secretion of foreign proteins from *Saccharomyces cerevisiae* directed by a-factor gene fusions," Proc. Natl. Acad. Sci. USA, 1984, 81:5330-5334.

(Continued)

*Primary Examiner*—Gary B Nickol
*Assistant Examiner*—Xiaozhen Xie
(74) *Attorney, Agent, or Firm*—Mary K. Hehman

(57) ABSTRACT

The invention is directed to purified and isolated novel human IL-1 epsilon polypeptides, the nucleic acids encoding such polypeptides, processes for production of recombinant forms of such polypeptides, antibodies generated against these polypeptides, fragmented peptides derived from these polypeptides, the use of such polypeptides and fragmented peptides in cellular and immune reactions and as molecular weight markers, the use of such polypeptides and fragmented peptides as controls for peptide fragmentation, and kits comprising these reagents.

12 Claims, 4 Drawing Sheets

OTHER PUBLICATIONS

Blume, et al., "Immature Transformed Rat Islet β-Cells Differentially Express C-Peptides Derived from the Genes Coding for Insulin I . . . ," Mol. Endocrinology, 1992, 6:299-307.

Bowie et al., "Deciphering the Message in Protein Sequence Tolerance to Amino Acid Substitutions," JSTOR: Science: New Series, 1990, 247(4948):1306-1310.

Brock, T.D. and Madigan, M.T., Biology of Microorganisms, (Prentice Hall, 6th Ed., Englewood Cliffs, NJ, (1991)), 76-77.

Brock, T.D. and Madigan, M.T., Biology of Microorganisms, (Prentice Hall, 6th Ed., Englewood Cliffs, NJ, (1991)), 300-301.

Brown, et al., "Characterization of Two Morphology Mutants of Autographa Californica Nuclear Polyhedrosis Virus with . . . Inclusion Bodies," J. Gen. Virol., 1980, 50:309-316.

Byrn et al.,"Biological properties of a CD4 immunoadhesin," Nature, 1990, 334:667-670.

Chang, et al., "Phenotypic expression in E. coli of a DNA sequence coding for mouse dihydrofolate reductase," Nature, 1978, 275(19):617-624.

Cleveland, et al., Peptide Mapping by Limited Proteolysis in Sodium Dodecyl Sulfate and Analysis by Gel Electrophoresis, J. of Biol. Chem., 1977, 252:1102-1106.

Colman, et al., "Effects of amino acid sequence changes on antibody-antigen interactions," Research in Immunology, 1994, 145:33-36.

Colotta et al., "Interleukin-1 Type II Receptor: A Decoy Target for IL-1 That Is Requlated by IL-4," Science, 1993, 261(5120):472-475.

Cosman, et al., "Cloning, sequence and expression of human interleukin-2 receptor," Nature, 1984, 312:768-771.

Cosman, et al., "High Level Stable Expression of Human Interleukin-2 Receptors in Mouse Cells . . . Low Affinity Interleukin-2 Binding Sites," Mol. Immunol., 1986, 23:935-941.

Craik, et al., "Use of Oligonucleotides for Site-Specific Mutagenesis," BioTechniques, Jan. 1985, 12-19.

Devereux, et al., "A Comprehensive set of sequence analysis programs for the VAX", Nucl. Acids Res.,1984, 12:387-395.

Eckerskorn, et al., "Identification of mouse brain proteins after two-dimensional electrophoresis and electroblotting . . . " Electrophoresis, 1988, 9:830-838.

Evans, et al., "Mapping Receptor Binding Sites in Interleukin (IL)-1 Receptor Antagonist and IL-1β by Site-directed Mutagenesis," J. of Biol. Chem., 1995, 270(19):11477-11483.

Felgner, et al., "Lipofection: A highly efficient, lipid-mediated DNA-tranfection procedure," Proc. Natl. Acad. Sci. USA, 1987, 84:7413-7417.

Fiers, et al., "Complete nucleotide sequence of SV40 DNA," Nature, 1978, 273:113-120.

Fleer, et al., "High-level secretion of correctly processed recombinant human interleukin-1β in Kluyveromyces lactis," 1991, Gene, 107:285-295.

Geysen, et al., "Cognitive Features of Continuous Antigenic Determinants," J. of Molecular Recognition, 1988, 1(1):32-41.

Gingeras, et al., "Nucleotide Sequences from the Adenovirus-2 Genome," Journal of Biological Chemistry, 1982, 257:13475-13491.

Gluzman, V., SV40-Transformed Simian Cells Support the Replication of Early SV40 Mutants, Jan. 1981, Cell, 23:175-182.

Goeddel, et al., "Direct expression in Escherichia coli of a DNA sequence coding for human growth hormone," Nature, 1979, 281:544-548.

Goeddel, et al., "Synthesis of human fibroblast interferon by E. coli," Nucl. Acids Res., 1980, 8:4057-4074.

Gribskov and Burgess, "Sigma factors from E. coli, B. subtilis, phage SP01, and phage T4 are homologous proteins," Nucl.Acids Res., 1986, 14:6745-6763.

Gross, E., "The Cyanogen Bromide Reaction," Methods in Enzymology, Enzyme Structure, vol. 11, Hirs, C.H.W., ed., (Academic Press, New YorK, (1967)), 11:238-255.

Hara and Miyajima, "Two distinct functional high affinity receptors for mouse interleukin-3 (IL-3)," EMBO J., 1992, 11(5):1875-1884.

Henzel, et al., "Identifying proteins from two-dimensional gels by molecular mass searching of peptide fragments in protein . . . " Proc. Natl. Acad. Sci. USA, 1993, 90:5011-5015.

Hess, et al., "Cooperation of Glycolytic Enzymes," J. Adv. Enzyme Reg., 1969, 7:149-167.

Hinnen, et al., "Transformation of yeast," Proc. Natl. Acad. Sci. USA, 1978, 75:1929-1933.

Hitzeman, et al., "Isolation and Cheracterization of the Yeast 3-Phosphoglycerokinase Gene (PGK) by an Immunological Screening . . . ," J. Biol. Chem., 1980, 255:1207-12080.

Holland, et al., "Isolation and Identification of Yeast Messenger Ribonucleic Acids Coding for Enolace . . . " Biochemistry, 1978, 17(23):4900-4907.

Hopp, et al., "A short polypeptide marker sequence useful for recombinant protein identification and purification," Bio/Technology, 1988, 6:1204-1210.

Jaroszewski, et al., "Fold prediction by a hierarchy of sequence, threading, and modeling methods," Protein Science, 1998, 7:1431-1440.

Kaufman, R. J., "Use of Recombinant DNA Technology . . . ," Large-Scale Mammalian Cell Culture Technology, Lubiniecki, A., ed. (Marcelo Dekker, Inc., NY, (1990)), pp. 15-69.

Kaufman, R. J., "Vectors Used for Expression in Mammalian Cells," Meth. in Enzymology, 1990, 185:487-510.

Kunkel, Thomas A., "Rapid and efficient site-specific mutagenesis without phenotypic selection," Proc. Natl. Acad. Sci. USA, 1985, 82:488-492.

Kunkel, Thomas A. et al., "Rapid and Efficient Site-Specific Mutagenesis without Phenotypic Selection," Methods in Enzymology, 1987, 154:367-382.

Kurjan, et al., "Structure of a Yeast Pheromone Gene (MFα): A Putative α-Factor Precursor Contains Four Tandem Copies of Mature α-Factor," Cell, 1982, 30:933-943.

Laemmli, U.K., "Cleavage of Structural Proteins during the Assembly of the Head of Bacteriophage T4," Nature, 1970, 277:680-685.

Larrick, et al., "Polymerase Chain Reaction Using Mixed Primers: Cloning of Human Monoclonal Antibody Variable Region Genes . . . ," Bio/Technology, 1989, 7:934-938.

Laskowski, et al., "Aqua and Procheck-NMR: Programs for checking the quality of protein structures solved by NMR," J. of Biomolecular NMR, 1996, 8:477-486.

Luckow and Summers, Trends in the Development of Baculovirus Expression Vectors, Bio/Technology, 1988, 6:47-55.

Maniatis, et al., Molecular Cloning: A Laboratory Manual, (Cold Spring Harbor Laboratory, Cold Spring Harbor, NY, (1982)), p. 412.

Masaki, et al., "Studies on a New Proteolytic Enzyme from Achromobacter Lyticus M497-1 I. Purification and Some Enzymatic . . . ", Biochimica et Biophysica Acta, 1981, 660:44-50.

Masaki, et al., "Studies on a New Proteolytic Enzyme from Achromobacter Lyticus M497-1 II. Specificity and Inhibition Studies . . . ", Biochim. et Biophys. Acta, 1981, 660:51-55.

Matsudaira, P., "Sequence from Picomole Quantities of Proteins Electroblotted onto Polyvinylidene Difluoride Membranes," J. of Biol. Chem., 1987, 262:10035-10038.

McMahan, et al., "A novel IL-1 receptor, cloned from B cells by mammalian expression, is expressed in many cell types," EMBO Journal, 1991, 10:2821-2832.

Morris, et al., "Expression Augmenting Sequence Element (EASE) . . . ," Animal Cell Technology, Carrondo et al., (eds.), (Kluwer Academic Pub., Netherlands, (1997)) 529-534.

Mosley, et al., "The Murine Interleukin-4 Receptor: Molecular Cloning and Characterization of Secreted and Membrane Bound Forms," Cell, 1989, 59:335-348.

Mosser, et al, "Use of a Dicistronic Expression Cassette Encoding the Green Fluorescent Protein for the Screening . . . ," Biotechniques, 1997, 22:150-161.

Needleman and Wunsch, "A General Method Applicable to the Search for Similarities in the Amino Acid Sequence of Two Proteins," J. Mol. Biol., 1970, 48:443-453.

Oh and Sarnow, "Gene regulation: translational initiation by internal ribosome binding," Current Opinion in Genetics and Development, 1993, 3:295-300.

Okayama and Berg, "A cDNA Cloning Vector that Permits Expression of cDNA Inserts in Mammalian Cells," Mol. Cell. Biol., 1983, 3:280-289.

Quentmeier, et al. "Cloning of human thymic stromal lymphopoietin (TSLP) and signaling mechanisms leading to proliferation," Leukemia, 2001, 15:1286-1292.

Ramesh, et al., "High-titer bicistronic retroviral vectors employing foot-and-mouth disease virus internal ribosome entry site," Nucleic Acids Research, 1996, 24:2697-2700.

Russell et al., "Nucleotide Sequence of the Yeast Alcohol Dehydrogenase II Gene," J. Biol. Chem., 1983, 258:2674-2682.

Sali, et al., "Evaluation of Comparative Protein Modeling by Modeller," Proteins: Structure, Function, and Genetics, 1995, 23:318-326.

Sambrook, et al., Molecular Cloning: A Laboratory Manual, 2nd Ed., vol. 1, (Cold Spring Harbor Laboratory Press, Cold Spring Harbor, (1989)), pp. 1.101-104.

Schatchard, G., "The Attractions of Proteins for Small Molecules and Ions," Ann. NY Acad. Sci., 1949, 51:660-672.

Schreuder, et al., "A new cytokine-receptor binding mode revealed by the crystal structure of the IL-1 receptor with an antagonist," Nature, 1997, 386:194-200.

Schwartz and Dayhoff, "Matrices for Detecting Distant Relationships," Atlas of Protein Sequence and Structure, (National Biomedical Res. Foundation, (1979)), pp. 353-358.

Smith, et al., "Four New Members Expand the Interleukin-1 Superfamily," J. Biol. Chem., 2000, 275(2) 1169-1175.

Smith and Waterman, "Comparison of Biosequences," Adv. Appl. Math., 1981, 2:482-489.

Stein and Cohen, "Oligodeoxynucleotides as Inhibitors of Gene Expression: A Review," Cancer Res., 1988, 48:2659-2668.

Thiede, et al., "Identification of human myocardial proteins separated by two-dimensional electrophoresis . . . " Electrophoresis, 1996, 17:588-599.

Urdal, et al., "Lymphokine Purification by Reversed-Phase High-Performance Liquid Chromatography," J. of Chromatog., 1984, 296:171-179.

Urlaub and Chasin, "Isolation of Chinese hamster cell mutants deficient in dihydrofolate reductase activity," Proc. Natl. Acad. Sci. USA, 1980, 77:4216-4220.

Van Den Berg, et al., Kluyveromyces as a Host for Heterologous Gene Expression: Expression and Secretion of Prochymosin, Bio/Technology, 1990, 8:135-139.

Van Der Krol, et al., "Modulation of Eukaryotic Gene Expression by Complementary RNA or DNA Sequences," BioTechniques, 1988, 6:958-976.

Vigers, "Crystal Structure of the type-1 interleukin-1 receptor complexed with interleukin-1β," Nature, 1997, 386:190-194.

Walder et al., "Oligodeoxynucleotide-directed mutagenesis using the yeast transformation system," Gene, 1986, 42:133-139.

Database EMBL. Entry MMA30324, Accession No. AA030324, Jan. 21, 1997, 2125184, Marra et al.

Dinarello, C.A., "Interleukin-1," *Cytokine and Growth Factor Review* vol. 8(4):253-265.

NAME: Human IL-1 epsilon DNA

Nucleotide sequence:

```
GAAAAGGATA TAATGGATTT GTACAACCAA CCCGAGCCTG TGAAGTCCTT
TCTCTTCTAC CACAGCCAGA GTGGCAGGAA CTCCACCTTC GAGTCTGTGG
CTTTCCCTGG CTGGTTCATC GCTGTCAGCT CTGAAGGAGG CTGTCCTCTC
ATCCTTACCC AAGAACTGGG GAAAGCCAAC ACTACTGACT TTGGGTTAAC
TATGCTGTTT TAA·
```
(SEQ ID NO:5)

```
ATGGAAAAAG CATTGAAAAT TGACACACCT CAGCAGGGGA GCATTCAGGA
TATCAATCAT CGGGTGTGGG TTCTTCAGGA CCAGACGCTC ATAGCAGTCC
CGAGGAAGGA CCGTATGTCT CCAGTCACTA TTGCCTTAAT CTCATGCCGA
CATGTGGAGA CCCTTGAGAA AGACAGAGGG AACCCCATCT ACCTGGGCCT
GAATGGACTC AATCTCTGCC TGATGTGTGC TAAAGTCGGG GACCAGCCCA
CACTGCAGCT GAAGGAAAAG GATATAATGG ATTTGTACAA CCAACCCGAG
CCTGTGAAGT CCTTTCTCTT CTACCACAGC AGAGTGGCA GGAACTCCAC
CTTCGAGTCT GTGGCTTTCC CTGGCTGGTT CATCGCTGTC AGCTCTGAAG
GAGGCTGTCC TCTCATCCTT ACCCAAGAAC TGGGGAAAGC CAACACTACT
GACTTTGGGT TAACTATGCT GTTTTAA
```
(SEQ ID NO:7)

```
ATGGAAAAAG CATTGAAAAT TGACACACCT CAGCGGGGGA GCATTCAGGA
TATCAATCAT CGGGTGTGGG TTCTTCAGGA CCAGACGCTC ATAGCAGTCC
CGAGGAAGGA CCGTATGTCT CCAGTCACTA TTGCCTTAAT CTCATGCCGA
CATGTGGAGA CCCTTGAGAA AGACAGAGGG AACCCCATCT ACCTGGGCCT
GAATGGACTC AATCTCTGCC TGATGTGTGC TAAAGTCGGG GACCAGCCCA
CACTGCAGCT GAAGGAAAAG GATATAATGG ATTTGTACAA CCAACCCGAG
CCTGTGAAGT CCTTTCTCTT CTACCACAGC AGAGTGGCA GGAACTCCAC
CTTCGAGTCT GTGGCTTTCC CTGGCTGGTT CATCGCTGTC AGCTCTGAAG
GAGGCTGTCC TCTCATCCTT ACCCAAGAAC TGGGGAAAGC CAACACTACT
GACTTTGGGT TAACTATGCT GTTTTAA
```
(SEQ ID NO:12)

FIGURE 1

NAME: Human IL-1 epsilon polypeptide

Translation in relevant reading frame (5' 3'):

EKDIMDLYNQ PEPVKSFLFY HSQSGRNSTF ESVAFPGWFI AVSSEGGCPL
ILTQELGKAN TTDFGLTMLF *
(SEQ ID NO:6)

MEKALKIDTP QQGSIQDINH RVWVLQDQTL IAVPRKDRMS PVTIALISCR
HVETLEKDRG NPIYLGLNGL NLCLMCAKVG DQPTLQLKEK DIMDLYNQPE
PVKSFLFYHS QSGRNSTFES VAFPGWFIAV SSEGGCPLIL TQELGKANTT
DFGLTMLF*
(SEQ ID NO:8)

MEKALKIDTP QRGSIQDINH RVWVLQDQTL IAVPRKDRMS PVTIALISCR
HVETLEKDRG NPIYLGLNGL NLCLMCAKVG DQPTLQLKEK DIMDLYNQPE
PVKSFLFYHS QSGRNSTFES VAFPGWFIAV SSEGGCPLIL TQELGKANTT
DFGLTMLF*
(SEQ ID NO:13)

FIGURE 2 human IL-1 epsilon 3' exon (top) vs. mouse IL-1 epsilon (long form) (bottom):
(64% percent identity)

```
 1 EKDIMDLYNQPEPVKSFLFYHSQSGRNSTFESVAFPGWFIAVSSEGGCPL 50
   .|:||.||.||||||.|||.|||.||||| |||||||.|||||.|.||.||
 1 EKDIMDLYNQPEPVKSFLFYHSQSGRNSTFESVAFPGWFIAVSSEGGCPL 50

29 EGNIMEMYNKKEPVKASLFYHKKSGTTSTFESAAFPGWFIAVCSKGSCPL 78 (SEQ ID NO: 10)

51 ILTQELGKANTTDFGLTML 69 (SEQ ID NO: 11)
   ||||||||.||. ..|||
79 ILTQELGEIFITDFEMIVV 97
```

FIGURE 3

```
 51 HVETLEKDRGNPIYLGLNGLNLCLMCAKVGDQ.PTLQLKEKDIMDLYNQP  99
              :  .         |   . .   |   . |  .|  .| |::| |.
  1 ..........MFRILVVVCGSCRTISSLQSQGKSKQFQEGNIMEMYNKK  39

100 EPVKSFLFYHSQSGRNSTFESVAFPGWFIAVSSEGGCPLILTQELGKANT 149
    ||||. ||||  .||    ||||| |||||||||  |.|  |||||||||.
 40 EPVKASLFYHKKSGTTSTFESAAFPGWFIAVCSKGSCPLILTQELGEIFI  89

150 TDFGLTMLF*  159        (SEQ ID NO:9)
    ||| :  .. |
 90 TDFEMIVVH*   99        (SEQ ID NO:2)
```

(53% similarity, 49% identity)

FIGURE 4

SEQUENCE LISTING

<160> NUMBER OF SEQ ID NOS: 13

<210> SEQ ID NO 1
<211> LENGTH: 297
<212> TYPE: DNA
<213> ORGANISM: Mus sp;

<400> SEQUENCE: 1
atgttcagga tcttagtagt cgtgtgtgga tcctgcagaa caatatcctc actgcagtcc      60
caaggaaaga gcaaacagtt ccaggaaggg aacataatgg aaatgtacaa caaaaaggaa     120
cctgtaaaag cctctctctt ctatcacaag aagagtggta caacctctac atttgagtct     180
gcagccttcc ctggttggtt catcgctgtc tgctctaaag ggagctgccc actcattctg     240
acccaagaac tgggggaaat cttcatcact gacttcgaga tgattgtggt acattaa       297

<210> SEQ ID NO 2
<211> LENGTH: 98
<212> TYPE: PRT
<213> ORGANISM: Mus sp.

<400> SEQUENCE: 2

Met Phe Arg Ile Leu Val Val Cys Gly Ser Cys Arg Thr Ile Ser
1               5                   10                  15

Ser Leu Gln Ser Gln Gly Lys Ser Lys Gln Phe Gln Glu Gly Asn Ile
                20                  25                  30

Met Glu Met Tyr Asn Lys Lys Glu Pro Val Lys Ala Ser Leu Phe Tyr
            35                  40                  45

His Lys Lys Ser Gly Thr Thr Ser Thr Phe Glu Ser Ala Ala Phe Pro
    50                  55                  60

Gly Trp Phe Ile Ala Val Cys Ser Lys Gly Ser Cys Pro Leu Ile Leu
65                  70                  75                  80

Thr Gln Glu Leu Gly Glu Ile Phe Ile Thr Asp Phe Glu Met Ile Val
                85                  90                  95

Val His

<210> SEQ ID NO 3
<211> LENGTH: 174
<212> TYPE: DNA
<213> ORGANISM: Mus sp;

<400> SEQUENCE: 3

```
atgttcagga tcttagtagt cgtgtgtgga tcctgcagaa caatatcctc actgcagtcc    60
caaggaaaga gcaaacagtt ccagtcacta ttaccttgct cccatgccaa tatctggaca   120
ctcttgagac gaacaggggg gatcccacgt acatgggagt gcaaaggccg atga         174
```

<210> SEQ ID NO 4
<211> LENGTH: 57
<212> TYPE: PRT
<213> ORGANISM: Mus sp.

<400> SEQUENCE: 4

```
Met Phe Arg Ile Leu Val Val Cys Gly Ser Cys Arg Thr Ile Ser
1               5                   10                  15

Ser Leu Gln Ser Gln Gly Lys Ser Lys Gln Phe Gln Ser Leu Leu Pro
            20                  25                  30

Cys Ser His Ala Asn Ile Trp Thr Leu Leu Arg Arg Thr Gly Gly Ile
        35                  40                  45

Pro Arg Thr Trp Glu Cys Lys Gly Arg
    50                  55
```

<210> SEQ ID NO 5
<211> LENGTH: 213
<212> TYPE: DNA
<213> ORGANISM: Homo sapiens;

<400> SEQUENCE: 5

```
gaaaaggata taatggattt gtacaaccaa cccgagcctg tgaagtcctt tctcttctac    60
cacagccaga gtggcaggaa ctccaccttc gagtctgtgg ctttccctgg ctggttcatc   120
gctgtcagct ctgaaggagg ctgtcctctc atccttaccc aagaactggg gaaagccaac   180
actactgact ttgggttaac tatgctgttt taa                                213
```

<210> SEQ ID NO 6
<211> LENGTH: 70
<212> TYPE: PRT
<213> ORGANISM: Homo sapiens

<400> SEQUENCE: 6

```
Glu Lys Asp Ile Met Asp Leu Tyr Asn Gln Pro Glu Pro Val Lys Ser
1               5                   10                  15

Phe Leu Phe Tyr His Ser Gln Ser Gly Arg Asn Ser Thr Phe Glu Ser
            20                  25                  30

Val Ala Phe Pro Gly Trp Phe Ile Ala Val Ser Ser Glu Gly Gly Cys
        35                  40                  45

Pro Leu Ile Leu Thr Gln Glu Leu Gly Lys Ala Asn Thr Thr Asp Phe
    50                  55                  60

Gly Leu Thr Met Leu Phe
65                  70
```

<210> SEQ ID NO 7
<211> LENGTH: 477
<212> TYPE: DNA
<213> ORGANISM: Homo sapiens;

<400> SEQUENCE: 7

```
atggaaaaag cattgaaaat tgacacacct cagcagggga gcattcagga tatcaatcat    60
cgggtgtggg ttcttcagga ccagacgctc atagcagtcc cgaggaagga ccgtatgtct   120
ccagtcacta ttgcccttaat ctcatgccga catgtggaga cccttgagaa agacagaggg   180
```

```
aaccccatct acctgggcct gaatggactc aatctctgcc tgatgtgtgc taaagtcggg    240
gaccagccca cactgcagct gaaggaaaag gatataatgg atttgtacaa ccaacccgag    300
cctgtgaagt cctttctctt ctaccacagc cagagtggca ggaactccac cttcgagtct    360
gtggctttcc ctggctggtt catcgctgtc agctctgaag gaggctgtcc tctcatcctt    420
acccaagaac tggggaaagc caacactact gactttgggt taactatgct gttttaa      477
```

<210> SEQ ID NO 8
<211> LENGTH: 158
<212> TYPE: PRT
<213> ORGANISM: Homo sapiens
<400> SEQUENCE: 8

```
Met Glu Lys Ala Leu Lys Ile Asp Thr Pro Gln Gln Gly Ser Ile Gln
1               5                   10                  15

Asp Ile Asn His Arg Val Trp Val Leu Gln Asp Gln Thr Leu Ile Ala
                20                  25                  30

Val Pro Arg Lys Asp Arg Met Ser Pro Val Thr Ile Ala Leu Ile Ser
            35                  40                  45

Cys Arg His Val Glu Thr Leu Glu Lys Asp Arg Gly Asn Pro Ile Tyr
    50                  55                  60

Leu Gly Leu Asn Gly Leu Asn Leu Cys Leu Met Cys Ala Lys Val Gly
65                  70                  75                  80

Asp Gln Pro Thr Leu Gln Leu Lys Glu Lys Asp Ile Met Asp Leu Tyr
                85                  90                  95

Asn Gln Pro Glu Pro Val Lys Ser Phe Leu Phe Tyr His Ser Gln Ser
            100                 105                 110

Gly Arg Asn Ser Thr Phe Glu Ser Val Ala Phe Pro Gly Trp Phe Ile
        115                 120                 125

Ala Val Ser Ser Glu Gly Gly Cys Pro Leu Ile Leu Thr Gln Glu Leu
    130                 135                 140

Gly Lys Ala Asn Thr Thr Asp Phe Gly Leu Thr Met Leu Phe
145                 150                 155
```

<210> SEQ ID NO 9
<211> LENGTH: 108
<212> TYPE: PRT
<213> ORGANISM: Homo sapiens
<400> SEQUENCE: 9

```
His Val Glu Thr Leu Glu Lys Asp Arg Gly Asn Pro Ile Tyr Leu Gly
1               5                   10                  15

Leu Asn Gly Leu Asn Leu Cys Leu Met Cys Ala Lys Val Gly Asp Gln
                20                  25                  30

Pro Thr Leu Gln Leu Lys Glu Lys Asp Ile Met Asp Leu Tyr Asn Gln
            35                  40                  45

Pro Glu Pro Val Lys Ser Phe Leu Phe Tyr His Ser Gln Ser Gly Arg
    50                  55                  60

Asn Ser Thr Phe Glu Ser Val Ala Phe Pro Gly Trp Phe Ile Ala Val
65                  70                  75                  80

Ser Ser Glu Gly Gly Cys Pro Leu Ile Leu Thr Gln Glu Leu Gly Lys
                85                  90                  95

Ala Asn Thr Thr Asp Phe Gly Leu Thr Met Leu Phe
            100                 105
```

<210> SEQ ID NO 10

```
<211> LENGTH: 69
<212> TYPE: PRT
<213> ORGANISM: Homo sapiens

<400> SEQUENCE: 10

Glu Lys Asp Ile Met Asp Leu Tyr Asn Gln Pro Glu Pro Val Lys Ser
1               5                   10                  15

Phe Leu Phe Tyr His Ser Gln Ser Gly Arg Asn Ser Thr Phe Glu Ser
            20                  25                  30

Val Ala Phe Pro Gly Trp Phe Ile Ala Val Ser Ser Glu Gly Gly Cys
        35                  40                  45

Pro Leu Ile Leu Thr Gln Glu Leu Gly Lys Ala Asn Thr Thr Asp Phe
    50                  55                  60

Gly Leu Thr Met Leu
65

<210> SEQ ID NO 11
<211> LENGTH: 77
<212> TYPE: PRT
<213> ORGANISM: Mus sp

<400> SEQUENCE: 11

Gln Gly Lys Ser Lys Gln Phe Gln Glu Gly Asn Ile Met Glu Met Tyr
1               5                   10                  15

Asn Lys Lys Glu Pro Val Lys Ala Ser Leu Phe Tyr His Lys Lys Ser
            20                  25                  30

Gly Thr Thr Ser Thr Phe Glu Ser Ala Ala Phe Pro Gly Trp Phe Ile
        35                  40                  45

Ala Val Cys Ser Lys Gly Ser Cys Pro Leu Ile Leu Thr Gln Glu Leu
    50                  55                  60

Gly Glu Ile Phe Ile Thr Asp Phe Glu Met Ile Val Val
65                  70                  75

<210> SEQ ID NO 12
<211> LENGTH: 477
<212> TYPE: DNA
<213> ORGANISM: Homo sapiens;

<400> SEQUENCE: 12
atggaaaaag cattgaaaat tgacacacct cagcggggga gcattcagga tatcaatcat      60
cgggtgtggg ttcttcagga ccagacgctc atagcagtcc cgaggaagga ccgtatgtct     120
ccagtcacta ttgccttaat ctcatgccga catgtggaga cccttgagaa agacagaggg     180
aaccccatct acctgggcct gaatggactc aatctctgcc tgatgtgtgc taaagtcggg     240
gaccagccca cactgcagct gaaggaaaag gatataatgg atttgtacaa ccaacccgag     300
cctgtgaagt cctttctctt ctaccacagc cagagtggca ggaactccac cttcgagtct     360
gtggctttcc ctggctggtt catcgctgtc agctctgaag gaggctgtcc tctcatcctt     420
acccaagaac tggggaaagc caacactact gactttgggt taactatgct gttttaa       477

<210> SEQ ID NO 13
<211> LENGTH: 158
<212> TYPE: PRT
<213> ORGANISM: Homo sapiens

<400> SEQUENCE: 13

Met Glu Lys Ala Leu Lys Ile Asp Thr Pro Gln Arg Gly Ser Ile Gln
1               5                   10                  15
```

-continued

```
Asp Ile Asn His Arg Val Trp Val Leu Gln Asp Gln Thr Leu Ile Ala
            20              25              30

Val Pro Arg Lys Asp Arg Met Ser Pro Val Thr Ile Ala Leu Ile Ser
        35              40              45

Cys Arg His Val Glu Thr Leu Glu Lys Asp Arg Gly Asn Pro Ile Tyr
    50              55              60

Leu Gly Leu Asn Gly Leu Asn Leu Cys Leu Met Cys Ala Lys Val Gly
65              70              75              80

Asp Gln Pro Thr Leu Gln Leu Lys Glu Lys Asp Ile Met Asp Leu Tyr
            85              90              95

Asn Gln Pro Glu Pro Val Lys Ser Phe Leu Phe Tyr His Ser Gln Ser
            100             105             110

Gly Arg Asn Ser Thr Phe Glu Ser Val Ala Phe Pro Gly Trp Phe Ile
        115             120             125

Ala Val Ser Ser Glu Gly Gly Cys Pro Leu Ile Leu Thr Gln Glu Leu
        130             135             140

Gly Lys Ala Asn Thr Thr Asp Phe Gly Leu Thr Met Leu Phe
145             150             155
```

HUMAN IL-1 EPSILON DNA AND POLYPEPTIDES

CROSS REFERENCE TO RELATED APPLICATIONS

This application is a divisional application of Ser. No. 10/986,744, filed Nov. 12, 2004, now U.S. Pat. No. 7,250,276, which is a divisional application of Ser. No. 09/763,498, filed May 15, 2001, now U.S. Pat. No. 6,949,359, which is the National Stage of International Application No. PCT/US99/18771, filed Aug. 20, 1999, which hereby claims the benefit of U.S. provisional applications Nos. 60/097,413, 60/098,595, and 60/099,974, filed Aug. 21, 1998, Aug. 31, 1998, and Sep. 11, 1998, respectively. The entire disclosures of these applications are relied upon and incorporated by reference herein.

BACKGROUND OF THE INVENTION

1. Field of the Invention

The invention is directed to purified and isolated novel human IL-1 epsilon polypeptides, the nucleic acids encoding such polypeptides, processes for production of recombinant forms of such polypeptides, antibodies generated against these polypeptides, fragmented peptides derived from these polypeptides, the use of such polypeptides and fragmented peptides in cellular and immune reactions and as molecular weight markers, the use of such polypeptides and fragmented peptides as controls for peptide fragmentation, and kits comprising these reagents.

2. Description of Related Art

Interleukin-1 (IL-1) is a member of a large group of cytokines whose primary function is to mediate immune and inflammatory responses. There are five known IL-1 family members which include IL-1 alpha (IL-1α), IL-1 beta (IL-β), IL-1 receptor antagonist (IL-1ra), IL-1 delta (IL-1δ, as disclosed in PCT US/99/00514), and IL-18 (previously known as IGIF and sometimes IL-1 gamma). IL-1 that is secreted by macrophages is actually a mixture of mostly IL-β and some IL-1 α (Abbas et al., 1994). IL-1α and IL-1β, which are first produced as 33 kD precursors that lack a signal sequence, are further processed by proteolytic cleavage to produce secreted active forms, each about 17 kD. Additionally, the 33 kD precursor of IL-1α is also active. Both forms of IL-1 are the products of two different genes located on chromosome 2. Although the two forms are less than 30 percent homologous to each other, they both bind to the same receptors and have similar activities.

IL-1ra, a biologically inactive form of IL-1, is structurally homologous to IL-1 and binds to the same receptors. Additionally, IL-1ra is produced with a signal sequence which allows for efficient secretion into the extracellular region where it competitively competes with IL-1 (Abbas et al., 1994).

The IL-1 family ligands bind to two IL-1 receptors that are members of the Ig superfamily. IL-1 receptors include the 80 kDa type I receptor (IL-1RI) and a 68 kDa type II receptor (IL-1RII). The ligands also bind to a soluble proteolytic fragment of IL-1RII (sIL-1RII) (Colotta et al., *Science* 261(5120):472-75, 1993).

The major source of IL-1 is the activated macrophage or mononuclear phagocyte. Other cells that produce IL-1 include epithelial and endothelial cells (Abbas et al., 1994). IL-1 secretion from macrophages occurs after the macrophage encounters and ingests gram-negative bacteria. Such bacteria contain lipopolysaccharide (LPS) molecules, also known as endotoxin, in the bacterial cell wall. LPS molecules are the active components that stimulate macrophages to produce tumor necrosis factor (TNF) and IL-1. In this case, IL-1 is produced in response to LPS and TNF production. At low concentrations, LPS stimulates macrophages and activates B-cells and other host responses needed to eliminate the bacterial infection; however, at high concentrations, LPS can cause severe tissue damage, shock, and even death.

The biological functions of IL-1 include activating vascular endothelial cells and lymphocytes, local tissue destruction, and fever (Janeway et al., 1996). At low levels, IL-1 stimulates macrophages and vascular endothelial cells to produce IL-6, upregulates molecules on the surface of vascular endothelial cells to increase leukocyte adhesion, and indirectly activates inflammatory leukocytes by stimulating mononuclear phagocytes and other cells to produce certain chemokines that activate inflammatory leukocytes. These IL-1 functions are crucial during low level microbial infections. However, if the microbial infection escalates, IL-1 acts systemically by inducing fever, stimulating mononuclear phagocytes to produce IL-1 and IL-6, increasing the production of serum proteins from hepatocytes, and activating the coagulation system. It is also known that IL-1 does not cause hemorrhagic necrosis of tumors or suppress bone marrow stem cell division. Nevertheless, IL-1 is lethal to humans at high concentrations.

Given the important function of IL-1, there is a need in the art for additional members of the IL-1 ligand family. In addition, in view of the continuing interest in protein research and the immune system, the discovery, identification, and roles of new proteins, such as human IL-1 epsilon and its receptors, are at the forefront of modern molecular biology and biochemistry. Despite the growing body of knowledge, there is still a need in the art for the identity and function of proteins involved in cellular and immune responses.

In yet another aspect of the invention, the identification of the primary structure, or sequence, of an unknown sample protein is the culmination of an arduous process of experimentation. In order to identify an unknown protein sample, the investigator can rely upon a comparison of the unknown protein sample to known peptides using a variety of techniques known to those skilled in the art. For instance, proteins are routinely analyzed using techniques such as electrophoresis, sedimentation, chromatography, and mass spectrometry.

Comparison of an unknown protein sample to polypeptides of known molecular weight allows a determination of the apparent molecular weight of the unknown protein sample (T. D. Brock and M. T. Madigan, *Biology of Microorganisms* 76-77 (Prentice Hall, 6$^{th}$ ed. 1991)). Protein molecular weight standards are commercially available to assist in the estimation of molecular weights of unknown protein samples (New England Biolabs Inc. Catalog: 130-131, 1995; J. L. Hartley, U.S. Pat. No. 5,449,758). However, the molecular weight standards may not correspond closely enough in size to the unknown sample protein to allow an accurate estimation of apparent molecular weight. The difficulty in estimation of molecular weight is compounded in the case of proteins that are subjected to fragmentation by chemical or enzymatic means (A. L. Lehninger, *Biochemistry* 106-108 (Worth Books, 2d ed. 1981)).

The unique nature of the composition of a protein with regard to its specific amino acid constituents results in a unique positioning of cleavage sites within the protein. Specific fragmentation of a protein by chemical or enzymatic cleavage results in a unique "peptide fingerprint" (D. W. Cleveland et al., *J. Biol. Chem.* 252:1102-1106, 1977; M. Brown et al., *J. Gen. Virol.* 50:309-316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76-77 (Prentice Hall, 6d ed. 1991)).

When a peptide fingerprint of an unknown protein is obtained, this can be compared to a database of known proteins to assist in the identification of the unknown protein (W. J. Henzel et al., *Proc. Natl. Acad. Sci. USA* 90:5011-5015, 1993; B. Thiede et al., *Electrophoresis* 1996, 17:588-599, 1996). A variety of computer software programs are accessible via the Internet to the skilled artisan for the facilitation of such comparisons, such as MultiIdent (Internet site: www.expasy.ch/sprot/multiident.html), PeptideSearch (Internet site: www.mann.embl-heiedelberg.de . . . deSearch/FR_PeptideSearchForm.html), and ProFound (Internet site: www.chait-sgi.rockefeller.edu/cgi-bin/prot-id-frag.html). These programs allow the user to specify the cleavage agent and the molecular weights of the fragmented peptides within a designated tolerance. The programs compare these molecular weights to protein databases' to assist in the elucidation of the identity of the sample protein. Accurate information concerning the number of fragmented peptides and the precise molecular weight of those peptides is required for accurate identification. Therefore, increasing the accuracy in the determination of the number of fragmented peptides and the precise molecular weight of those peptides should result in enhanced success in the identification of unknown proteins.

Fragmentation of proteins is further employed for the production of fragments for amino acid composition analysis and protein sequencing (P. Matsudiara, *J. Biol. Chem.* 262:10035-10038, 1987; C. Eckerskorn et al., *Electrophoresis* 1988, 9:830-838, 1988), particularly the production of fragments from proteins with a "blocked" N-terminus. In addition, fragmentation of proteins can be used in the preparation of peptides for mass spectrometry (W. J. Henzel et al., *Proc. Natl. Acad. Sci. USA* 90:5011-5015, 1993; B. Thiede et al., *Electrophoresis* 1996, 17:588-599, 1996), for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms* 300-301 (Prentice Hall, $6^{th}$ ed. 1991)), and for differentiation of homologous proteins (M. Brown et al., *J. Gen. Virol.* 50:309-316, 1980).

Thus, there also exists a need in the art for IL-1 polypeptides suitable for use in peptide fragmentation studies, for use in molecular weight measurements, and for use in protein sequencing using tandem mass spectrometry.

SUMMARY OF THE INVENTION

The invention aids in fulfilling these needs in the art by providing isolated human IL-1 epsilon nucleic acids and polypeptides encoded by these nucleic acids. Specifically, the invention encompasses an isolated human IL-1 epsilon nucleic acid molecule comprising the DNA sequences of SEQ ID NO:5, SEQ ID NO:7, and SEQ ID NO:12 and an isolated human IL-1 epsilon nucleic acid molecule encoding the amino acid sequence of SEQ ID NO:6, SEQ ID NO:8, and SEQ ID NO:13, as well as nucleic acid molecules complementary to these sequences. Both single-stranded and double-stranded RNA and DNA nucleic acid molecules are encompassed by the invention, as well as nucleic acid molecules that hybridize to a denatured, double-stranded DNA relating to SEQ ID NO:5, SEQ ID NO:7, or SEQ ID NO:12. Also encompassed are isolated nucleic acid molecules that are derived by in vitro mutagenesis from SEQ ID NO:5, SEQ ID NO:7, or SEQ ID NO:12, are degenerate from SEQ ID NO:5, SEQ ID NO:7, or SEQ ID NO:12, are allelic variants of human DNA of the invention, and are species homologs of DNA of the invention. The invention also encompasses recombinant vectors that direct the expression of these nucleic acid molecules and host cells transformed or transfected with these vectors. In addition, the invention encompasses methods of using the nucleic acid noted above in assays to identify chromosomes, map human genes, and study the immune system.

The invention also encompasses isolated polypeptides encoded by these nucleic acid molecules, synthetic polypeptides encoded by these nucleic acid molecules, and peptides and fragments of these polypeptides. Isolated polyclonal or monoclonal antibodies that bind to these polypeptides are also encompassed by the invention. The invention further encompasses methods for the production of IL-1 epsilon polypeptides, including culturing a host cell under conditions promoting expression and recovering the polypeptide from the culture medium. Especially, the expression of IL-1 epsilon polypeptides in bacteria, yeast, plant, insect, and animal cells is encompassed by the invention.

In general, the polypeptides of the invention can be used to study cellular processes such as immune regulation, cell proliferation, cell death, and inflammatory responses. In addition, the IL-1 epsilon ligand polypeptides, related IL-1 epsilon polypeptides, and fragments thereof, can be used to identify proteins associated with IL-1-like ligands and IL-1-like receptors.

In addition, assays utilizing IL-1 epsilon ligand polypeptides, related IL-1 epsilon polypeptides, and fragments thereof to screen for potential inhibitors of activity associated with polypeptide counter-structure molecules, and methods of using IL-1 epsilon ligand polypeptides, related IL-1 epsilon polypeptides, and fragments thereof as therapeutic agents for the treatment of diseases mediated by IL-1 epsilon ligand polypeptide counter-structure molecules are encompassed by the invention. Further, methods of using IL-1 epsilon ligand polypeptides, related IL-1 epsilon polypeptides, and fragments thereof in the design of inhibitors thereof are also an aspect of the invention.

The invention further includes a method for using these polypeptides and fragmented peptides thereof as molecular weight markers that allow the estimation of the molecular weight of a protein or a fragmented protein sample, as well as a method for the visualization of the molecular weight markers of the invention thereof using electrophoresis. The invention further encompasses methods for using the polypeptides of the invention and fragmented peptides thereof as markers for determining the isoelectric point of a sample protein, as well as controls for establishing the extent of fragmentation of a protein sample.

Further encompassed by this invention are kits to aid in these determinations.

BRIEF DESCRIPTION OF THE DRAWINGS

This invention will be more fully described with reference to the drawings in which:

FIG. 1 is the nucleotide sequences of human IL-1 epsilon DNA of the invention, SEQ ID NO:5, SEQ ID NO:7, and SEQ ID NO:12.

FIG. 2 is the amino acid sequence of polypeptides, SEQ ID NO:6, SEQ ID NO:8, and SEQ ID NO:13, encoded by the nucleotide sequences of SEQ ID NO:5, SEQ ID NO:7, and SEQ ID NO:12, respectively.

FIG. 3 depicts the amino acid homology between the 3' exon of human IL-1 epsilon and murine IL-1 epsilon (long form).

FIG. 4 depicts the amino acid homology between human IL-1 epsilon (amino acids 51-159) and murine IL-1 epsilon (long form).

DETAILED DESCRIPTION OF THE INVENTION

Interleukin-1 (IL-1) receptors are members of the large Ig superfamily of cytokine receptors, many of which mediate the response of immune system cells, in particular lymphocytes. In recent years, members of the family of ligands that bind to these receptors have been discovered at an accelerated pace. The increase in the number of known IL-1 ligands has been largely due to the advent of gene cloning and sequencing techniques. Amino acid sequences deduced from nucleotide sequences are considered to represent IL-1 ligands if they share homology with other known IL-1 ligands.

Mouse IL-1 epsilon is a homolog of the known IL-1 genes, IL-1α, IL-1β, IL-1δ (disclosed in PCT US/99/00514) and IL-1ra, and more recently, IL-18, previously known sometimes as IL-1 gamma. Mouse IL-1 epsilon was first identified by searching the EST database, and discovering an EST corresponding to mouse IL-1 epsilon (accession number AA030324). The entire open reading frame for the "long form" (see below) is contained in this EST.

```
Mouse IL-1 epsilon (Long Form) DNA Sequence
                                           (SEQ ID NO:1)
ATGTTCAGGA TCTTAGTAGT CGTGTGTGGA TCCTGCAGAA

CAATATCCTC ACTGCAGTCC CAAGGAAAGA GCAAACAGTT

CCAGGAAGGG AACATAATGG AAATGTACAA CAAAAAGGAA

CCTGTAAAAG CCTCTCTCTT CTATCACAAG AAGAGTGGTA

CAACCTCTAC ATTTGAGTCT GCAGCCTTCC CTGGTTGGTT

CATCGCTGTC TGCTCTAAAG GGAGCTGCCC ACTCATTCTG

ACCCAAGAAC TGGGGGAAAT CTTCATCACT GACTTCGAGA

TGATTGTGGT ACATTAA

Mouse IL-1 epsilon (Long Form) Amino Acid Sequence
                                           (SEQ ID NO:2)
MFRILVVVCG SCRTISSLQS QGKSKQFQEG NIMEMYNKKE

PVKASLFYHK KSGTTSTFES AAFPGWFIAV CSKGSCPLIL

TQELGEIFIT DFEMIVVH*
```

While showing homology to the IL-1 genes, mouse IL-1 epsilon is unusual in that the EST originally identified appeared to encode the C-terminal two-thirds of an IL-1-like molecule. In addition, during studies of the expression of IL-1 epsilon, it became apparent that there are two, alternatively spliced, forms of mRNA that encode proteins with identical N-termini but divergent C-termini. The longer of these two proteins was that encoded by the original EST. The shorter (sometimes called the "isoform") is approximately one-third the length of a typical IL-1 family molecule.

```
Mouse IL-1 epsilon (Short Form) DNA Sequence
                                           (SEQ ID NO:3)
ATGTTCAGGA TCTTAGTAGT CGTGTGTGGA TCCTGCAGAA

CAATATCCTC ACTGCAGTCC CAAGGAAAGA GCAAACAGTT

CCAGTCACTA TTACCTTGCT CCCATGCCAA TATCTGGACA

CTCTTGAGAC GAACAGGGGG GATCCCACGT ACATGGGAGT

GCAAAGGCCG ATGA

Mouse IL-1 epsilon (Short Form) Amino Acid
Sequence
                                           (SEQ ID NO:4)
MFRILVVVCG SCRTISSLQS QGKSKQFQSL LPCSHANIWT

LLRRTGGIPR TWECKGR *
```

These two proteins (the long and the short form), encoded by alternatively spliced versions of the same original RNA transcript, may associate non-covalently and thus form a "whole" IL-1-like molecule.

In any event, using as a probe the mixed cDNAs for mouse long-form and short-form IL-1 epsilon, human IL-1 epsilon has been identified by screening of a human genomic library. Sequencing of a clone obtained from the human genomic library reveals a stretch of DNA which contains an open reading frame, encoding a portion of a protein with high homology to mouse IL-1 epsilon in the same region. The open reading frame appears to be an exon (the 3' most exon of the coding region). The splice acceptor site at the 5' end of this exon is in the identical position to the splice acceptor site of the corresponding exon in mouse IL-1 epsilon.

The DNA and amino acid sequences of this exon corresponding to human IL-1 epsilon are set forth in SEQ ID NO:5 and SEQ ID NO:6, respectively.

```
Nucleotide Sequence of Human IL-1 epsilon DNA:
                                           (SEQ ID NO:5)
GAAAAGGATA TAATGGATTT GTACAACCAA CCCGAGCCTG

TGAAGTCCTT TCTCTTCTAC CACAGCCAGA GTGGCAGGAA

CTCCACCTTC GAGTCTGTGG CTTTCCCTGG CTGGTTCATC

GCTGTCAGCT CTGAAGGAGG CTGTCCTCTC ATCCTTACCC

AAGAACTGGG GAAAGCCAAC ACTACTGACT TTGGGTTAAC

TATGCTGTTT TAA
```

A preferred polypeptide encoded by the nucleic acid sequence is set forth below:

```
Amino Acid Sequence of Human IL-1 epsilon:
Translation in relevant reading frame (5' 3'):
                                           (SEQ ID NO:6)
EKDIMDLYNQ PEPVKSFLFY HSQSGRNSTF ESVAFPGWFI

AVSSEGGCPL ILTQELGKAN TTDFGLTMLF *
```

The full-length human IL-1 epsilon DNA sequence was isolated as described in Example I. The DNA and amino acid sequence of the full-length human IL-1 epsilon are set forth in SEQ ID NO:7 and SEQ ID NO:8, respectively.

```
Full-Length Nucleotide sequence of Human IL-1
epsilon DNA:
                                           (SEQ ID NO:7)
```

```
ATGGAAAAAG CATTGAAAAT TGACACACCT CAGCAGGGGA

GCATTCAGGA TATCAATCAT CGGGTGTGGG TTCTTCAGGA

CCAGACGCTC ATAGCAGTCC CGAGGAAGGA CCGTATGTCT

CCAGTCACTA TTGCCTTAAT CTCATGCCGA CATGTGGAGA

CCCTTGAGAA AGACAGAGGG AACCCCATCT ACCTGGGCCT

GAATGGACTC AATCTCTGCC TGATGTGTGC TAAAGTCGGG

GACCAGCCCA CACTGCAGCT GAAGGAAAAG GATATAATGG

ATTTGTACAA CCAACCCGAG CCTGTGAAGT CCTTTCTCTT

CTACCACAGC CAGAGTGGCA GGAACTCCAC CTTCGAGTCT

GTGGCTTTCC CTGGCTGGTT CATCGCTGTC AGCTCTGAAG

GAGGCTGTCC TCTCATCCTT ACCCAAGAAC TGGGGAAAGC

CAACACTACT GACTTTGGGT TAACTATGCT GTTTTAA

Full-Length Amino Acid Sequence of Human IL-1
epsilon:
Translation in relevant reading frame (5' to 3'):
                                      (SEQ ID NO:8)
MEKALKIDTP QQGSIQDINH RVWVLQDQTL IAVPRKDRMS

PVTIALISCR HVETLEKDRG NPIYLGLNGL NLCLMCAKVG

DQPTLQLKEK DIMDLYNQPE PVKSFLFYHS QSGRNSTFES

VAFPGWFIAV SSEGGCPLIL TQELGKANTT DFGLTMLF *
```

In addition, a single nucleotide polymorphism was identified in the human IL-1 epsilon gene. Specifically, the polymorphism comprises an adenosine to guanosine substitution at nucleotide 35. The polypeptide encoded by this polymorphic IL-1 epsilon gene has an arginine residue at position 12 rather than a glutamine residue. The DNA sequence of the human IL-1 epsilon gene containing this single nucleotide polymorphism is set forth in SEQ ID NO:12, and the full-length amino acid sequence corresponding to this polymorphic gene is set forth in SEQ ID NO:13.

```
Full-Length Nucleotide sequence of Polymorphic
Human IL-1 epsilon DNA:
                                     (SEQ ID NO:12)
ATGGAAAAAG CATTGAAAAT TGACACACCT CAGCGGGGA

GCATTCAGGA TATCAATCAT CGGGTGTGGG TTCTTCAGGA

CCAGACGCTC ATAGCAGTCC CGAGGAAGGA CCGTATGTCT

CCAGTCACTA TTGCCTTAAT CTCATGCCGA CATGTGGAGA

CCCTTGAGAA AGACAGAGGG AACCCCATCT ACCTGGGCCT

GAATGGACTC AATCTCTGCC TGATGTGTGC TAAAGTCGGG

GACCAGCCCA CACTGCAGCT GAAGGAAAAG GATATAATGG

ATTTGTACAA CCAACCCGAG CCTGTGAAGT CCTTTCTCTT

CTACCACAGC CAGAGTGGCA GGAACTCCAC CTTCGAGTCT

GTGGCTTTCC CTGGCTGGTT CATCGCTGTC AGCTCTGAAG

GAGGCTGTCC TCTCATCCTT ACCCAAGAAC TGGGGAAAGC

CAACACTACT GACTTTGGGT TAACTATGCT GTTTTAA

Full-Length Amino Acid Sequence of Human IL-1
epsilon:
Translation in relevant reading frame (5' to 3'):
                                     (SEQ ID NO:13)
MEKALKIDTP QRGSIQDINH RVWVLQDQTL IAVPRKDRMS

PVTIALISCR HVETLEKDRG NPIYLGLNGL NLCLMCAKVG

DQPTLQLKEK DIMDLYNQPE PVKSFLFYHS QSGRNSTFES

VAFPGWFIAV SSEGGCPLIL TQELGKANTT DFGLTMLF *
```

The discovery of this DNA encoding IL-1 epsilon enables the construction of expression vectors comprising nucleic acid sequences encoding IL-1 epsilon polypeptides of the invention; host cells transfected or transformed with the expression vectors; biologically active human IL-1 epsilon polypeptides and molecular weight markers as isolated and purified proteins; and antibodies immunoreactive with polypeptides of the invention.

Nucleic Acid Molecules

In a particular embodiment, the invention relates to certain isolated nucleotide sequences. A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual*, $2^{nd}$ ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Particularly preferred nucleotide sequences of the invention are SEQ ID NO:5, SEQ ID NO:7, and SEQ ID NO:12, as set forth above. The invention further encompasses isolated fragments and oligonucleotides derived from the nucleotide sequences of SEQ ID NO:5, SEQ ID NO:7, and SEQ ID NO:12. Nucleic acid sequences within the scope of the invention include isolated DNA and RNA sequences that hybridize to the native nucleotide sequences disclosed herein under conditions of moderate or severe stringency, and which encode polypeptides or fragments thereof of the invention. These isolated DNA and RNA sequences also include full length DNA or RNA molecules encoding for IL-1 epsilon polypeptides.

As used herein, conditions of moderate stringency, as known to those having ordinary skill in the art, and as defined by Sambrook et al. *Molecular Cloning: A Laboratory Manual*, $2^{nd}$ ed. Vol. 1, pp. 1.101-104, Cold Spring Harbor Laboratory Press, (1989), include use of a prewashing solution for the nitrocellulose filters 5× SSC, 0.5% SDS, 1.0 mM EDTA (pH 8.0), hybridization conditions of 50% formamide, 6× SSC at 42EC (or other similar hybridization solution, such as Stark's solution, in 50% formamide at 42EC), and washing conditions of about 60EC, 0.5× SSC, 0.1% SDS. Conditions of high stringency are defined as hybridization conditions as above, and with washing at 68EC, 0.2× SSC, 0.1% SDS. The skilled artisan will recognize that the temperature and wash solution salt concentration can be adjusted as necessary according to factors such as the length of the probe.

Due to the known degeneracy of the genetic code, wherein more than one codon can encode the same amino acid, a DNA sequence can vary from that shown in SEQ ID NO:5, SEQ ID NO:7, or SEQ ID NO:12, and still encode a polypeptide having the amino acid sequence of SEQ ID NO:6, SEQ ID NO:8, or SEQ ID NO:13, respectively. Such variant DNA sequences can result from silent mutations (e.g., occurring during PCR amplification) or can be the product of deliberate mutagenesis of a native sequence.

The invention thus provides equivalent isolated DNA sequences encoding polypeptides of the invention, selected from: (a) DNA derived from the coding region of a native mammalian gene; (b) cDNA comprising the nucleotide sequence of SEQ ID NO:5, SEQ ID NO:7, or SEQ ID NO:12; (c) DNA encoding the polypeptides of SEQ ID NO:6, SEQ ID NO:8, or SEQ ID NO:13; (d) DNA capable of hybridization to a DNA of (a), (b), or (c) under conditions of moderate stringency and which encodes polypeptides of the invention; and (e) DNA which is degenerate as a result of the genetic code to a DNA defined in (a), (b), (c), or (d) and which encodes polypeptides of the invention. Of course, polypeptides encoded by such equivalent DNA sequences are encompassed by the invention.

DNA that is equivalent to the DNA sequence of SEQ ID NO:5, SEQ ID NO:7, or SEQ ID NO:12 will hybridize under moderately stringent conditions to the double-stranded native DNA sequence that encode polypeptides comprising amino acid sequences of SEQ ID NO:6, SEQ ID NO:8, or SEQ ID NO:13. Examples of polypeptides encoded by such DNA, include, but are not limited to, polypeptide fragments and polypeptides comprising inactivated N-glycosylation site(s), inactivated protease processing site(s), or conservative amino acid substitution(s), as described below. Polypeptides encoded by DNA derived from other mammalian species, wherein the DNA will hybridize to the complement of the DNA of SEQ ID NO:5, SEQ ID NO:7, or SEQ ID NO:12, are also encompassed.

Expression

The nucleic acid sequence encoding polypeptides of the invention can be inserted into recombinant expression vectors using well known methods. The expression vectors include a DNA sequence of the invention operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the DNA sequence of the invention. Thus, a promoter nucleotide sequence is operably linked to a DNA sequence if the promoter nucleotide sequence controls the transcription of the DNA sequence of the invention. The ability to replicate in the desired host cells, usually conferred by an origin of replication, and a selection gene by which transformants are identified can additionally be incorporated into the expression vector.

In addition, sequences encoding appropriate signal peptides that are not naturally associated with polypeptides of the invention can be incorporated into expression vectors. For example, a DNA sequence for a signal peptide (secretory leader) can be fused in-frame to the nucleotide sequence of the invention so that the polypeptide is initially translated as a fusion protein comprising the signal peptide. A signal peptide that is functional in the intended host cells enhances extracellular secretion of the polypeptide. The signal peptide can be cleaved from the polypeptide upon secretion of polypeptide from the cell.

Suitable host cells for expression of polypeptides of the invention include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides of the invention using RNAs derived from DNA constructs disclosed herein.

Prokaryotic Systems

Prokaryotes include gram negative or gram positive organisms. Suitable prokaryotic host cells for transformation include, for example, *Escherichia coli, Bacillus subtilis, Salmonella typhimurium*, and various other species within the genera *Bacillus, Pseudomonas, Streptomyces*, and *Staphylococcus*. In a prokaryotic host cell, such as *Escherichia coli*, a polypeptide of the invention can include an N-terminal methionine residue to facilitate expression of the recombinant polypeptide in the prokaryotic host cell. The N-terminal Met can be cleaved from the expressed recombinant polypeptide.

Expression vectors for use in prokaryotic host cells also generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence of the invention are inserted into the pBR322 vector. Other commercially available vectors include, for example, pKK223-3 (Pharmacia Fine Chemicals, Uppsala, Sweden) and pGEM1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

The promoter sequences commonly used for recombinant prokaryotic host cell expression vectors include ∃-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776), and tac promoter (Maniatis, *Molecular Cloning: A Laboratory Manual*, Cold Spring Harbor Laboratory, p. 412, 1982). A particularly useful prokaryotic host cell expression system employs a phage 8 $P_L$ promoter and a cI857ts thermolabile repressor sequence. Plasmid vectors available from the American Type Culture Collection, which incorporate derivatives of the 8 $P_L$ promoter, include plasmid pHUB2 (resident in *E. coli* strain JMB9 (ATCC 37092)) and pPLc28 (resident in *E. coli* RR1 (ATCC 53082)).

The DNA of the invention can be cloned in-frame into the multiple cloning site of an ordinary bacterial expression vector. Ideally the vector contains an inducible promoter upstream of the cloning site, such that addition of an inducer leads to high-level production of the recombinant protein at a time of the investigator's choosing. For some proteins, expression levels can be boosted by incorporation of codons encoding a fusion partner (such as hexahistidine) between the promoter and the gene of interest.

For expression of the recombinant protein, the bacterial cells are propagated in growth medium until reaching a predetermined optical density. Expression of the recombinant protein is then induced, e.g., by addition of IPTG (isopropyl-b-D-thiogalactopyranoside), which activates expression of proteins from plasmids containing a lac operator/promoter. After induction (typically for 1-4 hours), the cells are harvested by pelleting in a centrifuge, e.g. at 5,000×G for 20 minutes at 4EC.

For recovery of the expressed protein, the pelleted cells may be resuspended in ten volumes of 50 mM Tris-HCl (pH 8)/1 M NaCl and then passed two or three times through a French press. Most highly-expressed recombinant proteins form insoluble aggregates known as inclusion bodies. Inclusion bodies can be purified away from the soluble proteins by pelleting in a centrifuge at 5,000×G for 20 minutes, 4EC. The inclusion body pellet is washed with 50 mM Tris-HCl (pH 8)/1% Triton X-100 and then dissolved in 50 mM Tris-HCl (pH 8)/8 M urea/0.1 M DTT. Any material that cannot be dissolved is removed by centrifugation (10,000×G for 20 minutes, 20EC). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM $Zn(OAc)_2$/1 mM GSSG/0.1 mM GSH. After refolding, purification can be carried out by a variety of chromatographic methods such as ion exchange or gel filtration. In some protocols, initial purification may be carried out before refolding. As an example, hexahistidine-tagged fusion proteins may be partially purified on immobilized nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Yeast Systems

Polypeptides of the invention alternatively can be expressed in yeast host cells, preferably from the *Saccharomyces* genus (e.g., *S. cerevisiae*). Other genera of yeast, such as *Pichia*, *K. lactis*, or *Kluyveromyces*, can also be employed. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980), or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73, 657 or in Fleer et. al., *Gene,* 107:285-195 (1991); and van den Berg et. al., *Bio/Technology,* 8:135-139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* can be constructed by inserting DNA sequences from pBR322 for selection and replication in *E. coli* ($Amp^r$ gene and origin of replication) into the above-described yeast vectors.

The yeast ∀-factor leader sequence can be employed to direct secretion of a polypeptide of the invention. The ∀-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324, 274. Other leader sequences suitable for facilitating secretion of recombinant polypeptides from yeast hosts are known to those of skill in the art. A leader sequence can be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 µg/ml adenine, and 20 µg/ml uracil.

Yeast host cells transformed by vectors containing ADH2 promoter sequence can be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian and Insect Systems

Alternatively, mammalian or insect host cell culture systems can be employed to express recombinant polypeptides of the invention. Baculovirus systems for production of heterologous proteins in insect cells are reviewed by Luckow and Summers, *Bio/Technology* 6:47 (1988). Established cell lines of mammalian origin also can be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line (ATCC CRL 10478) derived from the African green monkey kidney cell line CVI (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture,* 1990, pp. 15-69). Additional protocols using commercially available reagents, such as Lipofectamine (Gibco/BRL) or Lipofectamine-Plus, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. *Molecular Cloning: A Laboratory Manual,* $2^{nd}$ ed. Vol. 1-3, Cold Spring Harbor Laboratory Press, 1989. Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in U.S. patent application Ser. No. 07/701,415, filed May 16, 1991, incorporated by reference herein. The vectors can be derived from retroviruses. In place of the native signal sequence, a heterologous signal sequence can be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367, 566; the type I IL-1 receptor signal peptide described in U.S. Pat. No. 4,968,607; and the type II IL-1 receptor signal peptide described in EP 460,846.

Another useful expression vector, pFLAG, can be used. FLAG technology is centered on the fusion of a low molecular weight (1kD), hydrophilic, FLAG marker peptide to the N-terminus of a recombinant protein expressed by the pFLAG-1™ Expression Vector (1) (obtained from IBI Kodak).

Polypeptides of the Invention

As noted above, the present invention also includes isolated and purified polypeptides. As used herein, the "polypeptides" of the invention refers to a genus of polypeptides that further encompasses proteins having the amino acid sequence of SEQ ID NO: 6, SEQ ID NO:8, or SEQ ID NO:13, as well as those proteins having a high degree of similarity (at least 90% homology) with such amino acid sequences and which proteins are biologically active. In addition, polypeptides of the invention refers to the gene products of the nucleotides of SEQ ID NO:5, SEQ ID NO:7, and SEQ ID NO:12.

Isolation and Purification

The term "isolated and purified" as used herein, means that the polypeptides or fragments of the invention are essentially free of association with other proteins or polypeptides, for example, as a purification product of recombinant host cell culture or as a purified product from a non-recombinant source. The term "substantially purified" as used herein, refers to a mixture that contains polypeptides or fragments of the invention and is essentially free of association with other proteins or polypeptides, but for the presence of known proteins that can be removed using a specific antibody, and which substantially purified polypeptides or fragments thereof can be used as molecular weight markers. The term "purified" refers to either the "isolated and purified" form of polypeptides of the invention or the "substantially purified" form of polypeptides of the invention, as both are described herein.

An isolated and purified polypeptide according to the invention can be produced by recombinant expression systems as described above or purified from naturally occurring cells.

In one preferred embodiment, the expression of recombinant IL-1 epsilon polypeptides can be accomplished utilizing fusions of sequences encoding IL-1 epsilon polypeptides to sequences encoding another polypeptide to aid in the purification of polypeptides of the invention. An example of such a fusion is a fusion of sequences encoding an IL-1 epsilon polypeptide to sequences encoding the product of the malE gene of the pMAL-c2 vector of New England Biolabs, Inc. Such a fusion allows for affinity purification of the fusion protein, as well as separation of the maltose binding protein portion of the fusion protein from the polypeptide of the invention after purification.

The insertion of DNA encoding the IL-1 epsilon polypeptide into the pMAL-c2 vector can be accomplished in a variety of ways using known molecular biology techniques. The preferred construction of the insertion contains a termination codon adjoining the carboxyl terminal codon of the polypeptide of the invention. In addition, the preferred construction of the insertion results in the fusion of the amino terminus of the polypeptide of the invention directly to the carboxyl terminus of the Factor Xa cleavage site in the pMAL-c2 vector. A DNA fragment can be generated by PCR using DNA of the invention as the template DNA and two oligonucleotide primers. Use of the oligonucleotide primers generates a blunt-ended fragment of DNA that can be isolated by conventional means. This PCR product can be ligated together with pMAL-p2 (digested with the restriction endonuclease Xmn I) using conventional means. Positive clones can be identified by conventional means. Induction of expression and purification of the fusion protein can be performed as per the manufacturer's instructions and as noted above. This construction facilitates a precise separation of the polypeptide of the invention from the fused maltose binding protein utilizing a simple protease treatment as per the manufacturer's instructions. In this manner, purified IL-1 epsilon polypeptide can be obtained. Furthermore, such a constructed vector can be easily modified using known molecular biology techniques to generate additional fusion proteins. It is understood, of course, that many different vectors and techniques, as noted above, can be used for the expression and purification of polypeptides of the invention and that this embodiment in no way limits the scope of the invention.

Recombinant protein produced in bacterial culture is usually isolated by initial disruption of the host cells by any convenient method (including freeze-thaw cycling, sonication, mechanical disruption, or use of cell lysing agents), centrifugation, extraction from cell pellets if an insoluble polypeptide, or from the supernatant fluid if a soluble polypeptide, followed by one or more concentration, salting-out, ion exchange, affinity purification or size exclusion chromatography steps. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable polypeptide-binding proteins are anti-polypeptide antibodies, and other proteins that are capable of high-affinity binding of polypeptides of the invention. A preferred polypeptide-binding protein is an anti-polypeptide monoclonal antibody.

In a preferred embodiment, transformed yeast host cells are employed to express polypeptides of the invention as a secreted polypeptide in order to simplify purification. Secreted recombinant polypeptide from a yeast host cell fermentation can be purified by methods analogous to those disclosed by Urdal et al. (*J. Chromatog.* 296:171, 1984) (relating to the use of two sequential, reversed-phase HPLC steps for purification).

Variants

The invention also includes variants of the polypeptides of the invention. A polypeptide "variant" as referred to herein means a polypeptide substantially homologous to native polypeptides of the invention, but which has an amino acid sequence different from that of native polypeptides (human, murine or other mammalian species) of the invention because of one or more deletions, insertions or substitutions. The variant amino acid sequence preferably is at least 80% identical to a native polypeptide amino acid sequence. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. The percent identity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring variants are also encompassed by the invention. Examples of such variants are proteins that result from alternate mRNA splicing events, proteolytic cleavage of the IL-1 epsilon polypeptides, or transcription/translation from different alleles. Variations attributable to proteolysis include, for example, differences in the N or C-termini upon expression in different types of host cells, due to proteolytic removal of one or more terminal amino acids from the polypeptides (generally from 1-5 terminal amino acids) of the invention.

Oligomers

The polypeptides of the invention can also exist as oligomers, such as covalently linked or non-covalently linked dimers or trimers. Oligomers can be linked by disulfide bonds formed between cysteine residues on different polypeptides.

In one embodiment of the invention, a polypeptide dimer is created by fusing polypeptides of the invention to the Fc region of an antibody (e.g., IgG1) in a manner that does not interfere with the biological activity of these polypeptides. The Fc region preferably is fused to the C-terminus of a soluble polypeptide of the invention, to form an Fc fusion or an Fc polypeptide. The terms "Fc fusion protein" or "Fc polypeptides" as used herein includes native and mutein forms, as well as truncated Fc polypeptides containing the hinge region that promotes dimerization. Exemplary methods of making Fc polypeptides set forth above are disclosed in U.S. Pat. Nos. 5,426,048 and 5,783,672, both of which are incorporated herein by reference.

General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the polypeptide:Fc fusion protein of the invention is inserted into an appropriate expression vector. Polypeptide:Fc fusion proteins are allowed to assemble much like antibody molecules, whereupon interchain disulfide bonds form between Fc polypeptides, yielding divalent polypeptides of the invention. If fusion proteins are made with both heavy and light chains of an antibody, it is possible to form a polypeptide oligomer with as many as four polypeptides extracellular regions. Alternatively, one can link two soluble polypeptide domains with a peptide linker.

Alterations

As stated above, the invention provides isolated and purified polypeptides, and fragments thereof, both recombinant and non-recombinant. Variants and derivatives of native polypeptides can be obtained by mutations of nucleotide sequences coding for native polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

Polypeptides of the invention can also be modified to create polypeptide derivatives by forming covalent or aggregative conjugates with other chemical moieties, such as glycosyl groups, polyethylene glycol (PEG) groups, lipids, phosphate, acetyl groups and the like. Covalent derivatives of polypeptides of the invention can be prepared by linking the chemical moieties to functional groups on polypeptide amino acid side chains or at the N-terminus or C-terminus of a polypeptide of the invention or the extracellular domain thereof. Other derivatives of polypeptides within the scope of this invention include covalent or aggregative conjugates of these polypeptides or peptide fragments with other proteins or polypeptides, such as by synthesis in recombinant culture as N-terminal or C-terminal fusions. For example, the conjugate can comprise a signal or leader polypeptide sequence (e.g. the ∀-factor leader of *Saccharomyces*) at the N-terminus of a polypeptide of the invention. The signal or leader peptide co-translationally or post-translationally directs transfer of the conjugate from its site of synthesis to a site inside or outside of the cell membrane or cell wall.

Polypeptide conjugates can also comprise peptides added to facilitate purification and identification of polypeptides of the invention. Such peptides include, for example, poly-His or the antigenic identification peptides described in U.S. Pat. No. 5,011,912 and in Hopp et al., *Bio/Technology* 6:1204, 1988.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, equivalent DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Fragments and Uses Thereof

In yet another aspect of the invention, the polypeptides of the invention can be subjected to fragmentation into peptides by chemical and enzymatic means. The fragments so produced may be used for a variety of purposes, including molecular weight markers and isoelectric point markers. The polypeptides and peptide fragments can also be used for the analysis of the degree of fragmentation. Thus, the invention also includes these polypeptides and peptide fragments, as well as kits to aid in the determination of the apparent molecular weight and isoelectric point of a sample protein and kits to assess the degree of fragmentation of a sample protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238-255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44-50, 1981; T. Masaki et al., *Biochim. Biophys. Acta* 660:51-55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102-1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide. Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

Because the unique amino acid sequence of each piece specifies a molecular weight, these pieces can thereafter serve as molecular weight markers using such analysis techniques to assist in the determination of the molecular weight of a sample protein, polypeptides or fragments thereof. The molecular weight markers of the invention serve particularly well as molecular weight markers for the estimation of the apparent molecular weight of sample proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680-685, 1970). Conventionally, the method uses two separate lanes of a gel containing sodium dodecyl sulfate and a concentration of acrylamide between 6-20%. The ability to simultaneously resolve the marker and the sample under identical conditions allows for increased accuracy. It is understood, of course, that many different techniques can be used for the determination of the molecular weight of a sample protein using polypeptides of the invention, and that this embodiment in no way limits the scope of the invention.

In addition, the polypeptides and fragmented peptides of the invention possess unique charge characteristics and, therefore, can serve as specific markers to assist in the determination of the isoelectric point of a sample protein, polypeptides, or fragmented peptide using techniques such as isoelectric focusing. These polypeptide or fragmented peptide markers serve particularly well for the estimation of apparent isoelectric points of sample proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the sample protein under identical conditions allows for increased accuracy in the determination of the apparent isoelectric point of the sample protein. This is of particular interest in techniques, such as two dimensional electrophoresis (T. D. Brock and M. T. Madigan, *Biology of Microorganisms* 76-77 (Prentice Hall, 6$^{th}$ ed. 1991)), where the nature of the procedure dictates that any markers should be resolved simultaneously with the sample protein. In addition, with such methods, these polypeptides and fragmented peptides thereof can assist in the determination of both the isoelectric point and molecular weight of a sample protein or fragmented peptide.

Polypeptides and fragmented peptides can be visualized using two different methods that allow a discrimination between the sample protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the sample protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The sample protein is also visualized by using a conventional staining procedure. The molar excess of sample protein to polypeptide or fragmented peptide molecular weight markers of the invention is such that the conventional staining procedure predominantly detects the sample protein. The level of these polypeptide or fragmented peptide molecular weight markers is such as to allow little or no detection of these markers by the conventional staining method. The preferred molar excess of sample protein to polypeptide molecular weight markers of the invention is between 2 and 100,000 fold. More preferably, the preferred molar excess of sample protein to these polypeptide molecular weight markers is between 10 and 10,000 fold and especially between 100 and 1,000 fold.

It is understood of course that many techniques can be used for the determination and detection of molecular weight and isoelectric point of a sample protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252: 1102-1106, 1977), such as by altering the time or temperature of the fragmentation reaction, can be used as a control for the extent of cleavage of a sample protein. For example, cleavage of the same amount of polypeptide and sample protein under identical conditions can allow for a direct comparison of the extent of fragmentation. Conditions that result in the complete fragmentation of the polypeptide can also result in complete fragmentation of the sample protein.

As to the specific use of the polypeptides and fragmented peptides of the invention as molecular weight markers, the fragmentation of a preferred polypeptide of the invention with cyanogen bromide generates a unique set of fragmented peptide molecular weight markers with molecular weights of approximately 6933, 625, and 238 Daltons in the absence of glycosylation. An additional fragment of 149 Daltons results if the initiating methionine is present. Cleavage of SEQ ID NO:8 by cyanogen bromide generates fragments having molecular weights of 149.2, 260.3, 2017.4, 3954.6, 4442.1, and 6932.7. Cleavage of SEQ ID NO:13 by cyanogen bromide generates fragments having molecular weights of 149.2, 260.3, 2017.4, 3954.6, 4470.1, and 6932.7. The distribution of methionine residues determines the number of amino acids in each peptide and the unique amino acid composition of each peptide determines its molecular weight.

In addition, the preferred isolated and purified polypeptides of the invention (SEQ ID NO:6, SEQ ID NO:8, and SEQ ID NO:13) have calculated molecular weights of approximately 7810 (7941 Daltons after the addition of a methionine at position 1), 17684, and 17712 Daltons, respectively, in the absence of glycosylation. The observed molecular weights of known IL-1 polypeptides include 17, 25, 31, 33, and 35 kDa, and thus provide a range of molecular weights for use in these determinations.

Where an intact protein is used, the use of these polypeptide molecular weight markers allows increased accuracy in the determination of apparent molecular weight of proteins that have apparent molecular weights close to 7810, 17684, or 17712 Daltons. Where fragments are used, there is increased accuracy in determining molecular weight over the range of the molecular weights of the fragment.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the sample protein by chemical or enzymatic cleavage. Kits can further contain antibodies directed against polypeptides or fragments thereof of the invention.

Sense and Antisense Oligonucleotides

In yet another embodiment of the invention, antisense or sense oligonucleotides comprising a single-stranded nucleic acid sequence (either RNA or DNA) capable of binding to a target mRNA sequence (forming a duplex) or to the sequence in the double-stranded DNA helix (forming a triple helix) can be made according to the invention. Antisense or sense oligonucleotides, according to the present invention, comprise a fragment of the coding region of cDNA (SEQ ID NO:5, SEQ ID NO:7, or SEQ ID NO:12). Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of complexes that block translation (RNA) or transcription (DNA) by one of several means, including enhanced degradation of the duplexes, premature termination of transcription or translation, or by other means. The antisense oligonucleotides thus can be used to block expression of polypeptides of the invention. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation), but retain sequence specificity to be able to bind to target nucleotide sequences. Other examples of sense or antisense oligonucleotides include those oligonucleotides that are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes can be attached to sense or antisense oligonucleotides to modify binding specificities of the antisense or sense oligonucleotide for the target nucleotide sequence.

Antisense or sense oligonucleotides can be introduced into a cell containing the target nucleic acid sequence by any gene transfer method, including, for example, CaPO$_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Alternatively, sense or antisense oligonucleotides also can be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

In yet another embodiment, a sense or an antisense oligonucleotide can be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Chromosome Mapping

In still another embodiment, oligonucleotides representing all or a portion of SEQ ID NO:5, SEQ ID NO:7, or SEQ ID NO:12 can be used by those skilled in the art using well-known techniques to identify the human chromosome 2, and the specific locus thereof, that contains the DNA of IL-1 family members, for example, IL-1 epsilon. As set forth below, SEQ ID NO:5, SEQ ID NO:7, and SEQ ID NO:12 have been mapped by radiation hybrid mapping to the long arm (2q) region of chromosome 2. That region is associated with specific diseases which include but are not limited to glaucoma, ectodermal dysplasia, insulin-dependent diabetes mellitus, wrinkly skin syndrome, T-cell leukemia/lymphoma, asthma, and tibial muscular dystrophy. Thus, SEQ ID NO:5, SEQ ID NO:7, SEQ ID NO:12, or a fragment of these sequences can be used by one skilled in the art using well-known techniques to study the above described diseases and other abnormalities relating to chromosome 2. This would enable one to distinguish conditions in which this marker is rearranged or deleted. In addition, SEQ ID NO:5, SEQ ID NO:7, SEQ ID NO:12, or a fragment thereof can be used as a positional marker to map other human genes of unknown location.

Therapeutic and Research Uses

Another embodiment of the invention relates to therapeutic uses of IL-1 epsilon. IL-1 ligands play a central role in protection against infection and in promoting immune and inflammatory responses, which includes cellular signal transduction, activating vascular endothelial cells and lymphocytes, induction of inflammatory cytokines, acute phase proteins, hematopoiesis, fever, bone resorption, prostaglandins, metalloproteinases, and adhesion molecules. With the continued increase in the number of known IL-1 family members, a suitable classification scheme is one based on comparing polypeptide structure as well as function (activation and regulatory properties). Thus, IL-1 epsilon, like IL-1α, IL-1β, and IL-18, is likely involved in many of the functions noted above. In addition, IL-1 epsilon is likely involved in promoting inflammatory responses and, therefore, may be integrally involved in the causation and maintenance of inflammatory and/or autoimmune diseases such as rheumatoid arthritis, inflammatory bowel disease, and psoriasis. As such, alterations in the expression and/or activation of IL-1 family members such as IL-1 epsilon can have profound effects on a plethora of cellular processes, including, but not limited to, activation or inhibition of cell specific responses, proliferation, and inflammatory reactions based on changes in signal transduction.

Accordingly, IL-1 epsilon has therapeutic uses, such as protecting against infection and generating immune and inflammatory responses in individuals whose immune and inflammatory responses are inappropriate or nonresponsive. For example, IL-1 epsilon may be useful in stimulating the immune system of individuals whose immune system is immunosuppressed. Similarly, because IL-1 epsilon likely promotes inflammatory responses and is involved in the causation and maintenance of inflammatory and/or autoimmune diseases, antagonists of IL-1 epsilon are useful in inhibiting or treating inflammatory and/or autoimmune disease.

IL-1 mediated cellular signaling often involves a molecular activation cascade, during which a receptor propagates a ligand-receptor mediated signal by specifically activating intracellular kinases which phosphorylate target substrates, resulting in the activation of the transcription factor NFkB and the protein kinases Jun N-terminal kinase and p38 map kinase. These substrates can themselves be kinases which become activated following phosphorylation. Alternatively, they can be adaptor molecules that facilitate down-stream signaling through protein-protein interaction following phosphorylation.

IL-1 epsilon may act as an antagonist and have an inhibitory effect on immune responses and inflammatory responses. For example, IL-1 epsilon may have a function similar to that of IL-1ra such that isolated and purified IL-1 epsilon polypeptides or fragments thereof of the invention can be useful as therapeutic agents in inhibiting signaling and treating inflammatory diseases and/or autoimmune diseases. However, given the data presented in Example III, below, it is more likely that IL-1 epsilon is an agonist, such as, for example IL-1α or IL-18. As stated above, such agonists are useful in promoting immune and inflammatory responses in individuals whose own immune systems are inappropriately under responsive. For purposes of antagonizing IL-1 epsilon activity, inhibitors of IL-1 epsilon can be engineered or designed using techniques known in the art. Polypeptides of the present invention, including IL-1 epsilon inhibitors, can be introduced into the extracellular environment by well-known means, such as by administering the protein intravenously or by coupling it to a monoclonal antibody targeted to a specific cell type, to thereby affect signaling.

When used as a therapeutic agent, polypeptides of the invention can be formulated into pharmaceutical compositions according to known methods. The polypeptides can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain the polypeptides complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of polypeptides of the invention.

The dosage of the composition can be readily determined by those of ordinary skill in the art. The amount to be administered and the frequency of administration can be determined empirically and will take into consideration the age and size of the patient being treated, as well as the malady being treated.

Treatment comprises administering the composition by any method familiar to those of ordinary skill in the art, including intravenous, intraperitoneal, intracorporeal injection, intra-articular, intraventricular, intrathecal, intramuscular, subcutaneous, topically, tonsillar, intranasally, intravaginally, and orally. The composition may also be given locally, such as by injection into the particular area, either intramuscularly or subcutaneously.

In addition, the DNA, polypeptides, and antibodies against polypeptides of the invention can be used as reagents in a variety of research protocols. A sample of such research protocols are given in Sambrook et al. *Molecular Cloning: A Laboratory Manual*, 2$^{nd}$ ed. Vol. 1-3, Cold Spring Harbor Laboratory Press, (1989). For example, these reagents can serve as markers for cell-specific or tissue-specific expression of RNA or proteins. Similarly, these reagents can be used to investigate constitutive and transient expression of RNA or polypeptides. As noted above, the DNA can be used to determine the chromosomal location of DNA and to map genes in relation to this chromosomal location. The DNA can also be used to examine genetic heterogeneity and heredity through the use of techniques such as genetic fingerprinting, as well as to identify risks associated with genetic disorders. The DNA can be further used to identify additional genes related to the DNA and to establish evolutionary trees based on the comparison of sequences. The DNA and polypeptides can be used to select for those genes or proteins that are homologous to the DNA or polypeptides, through positive screening procedures such as Southern blotting and immunoblotting and through negative screening procedures such as subtraction.

Further, because IL-1 epsilon is a ligand, it takes part in protein-protein interactions with at least one or more proteins, i.e. its receptor(s). Thus, the polypeptides and fragments of the invention can be used as reagents to identify (a) proteins that the polypeptide regulates, and (b) proteins with which it might interact. Therefore, IL-1 epsilon ligands or polypeptides comprising portions of an IL-1 epsilon ligand could be used by coupling recombinant protein to an affinity matrix, or by using them as "baits" in the yeast 2-hybrid system according to well established molecular biology techniques, to identify proteins that interact directly with the polypeptide of the invention. Further, the IL-1 epsilon polypeptides and fragments of the present invention find use in studies directed toward discovering IL-1 receptors and/or IL-1 epsilon receptors. For example, IL-1 epsilon polypeptides and IL-1 epsilon polypeptide fragments can be used in binding studies to identify receptor-expressing cells. Suitable binding studies are known in the art and are well within the knowledge of those skilled in the art. Similarly, the IL-1 epsilon polypeptides and polypeptide fragments of the present invention find additional uses in cloning receptors using expression cloning techniques.

The polypeptides and fragments thereof can also be used as reagents in the study of signaling pathways utilized by IL-1 and IL-1R homologs or family members, and/or in blocking those signaling pathways. Such novel IL-1 receptor homologs can be specifically used as reagents to identify novel molecules involved in signal transduction pathways, characterize cell and tissue expression, understand their roles in development, immune, and inflammatory responses, and identify regulatory molecules and physiologically relevant protein substrates.

Alternatively, polypeptides of the invention could be engineered prior to expression with a tag such as poly-His or FLAG, then be expressed and purified using either nickel chelate chromatography or anti-FLAG antibody coupled to a resin, respectively. Once bound to the resin, the polypeptide of the invention could be covalently attached using a bifunctional cross-linking agent using well established techniques. The covalently bound polypeptide to the resin could then be used to purify molecules from cell lysates or cell supernatants (following treatment with various reagent) through their affinity for the polypeptide of the invention.

Antibodies

Within the therapeutic and research aspects of the invention, polypeptides of the invention, and peptides based on the amino acid sequence thereof, can be utilized to prepare antibodies that specifically bind to the polypeptides. The term "antibodies" is meant to include polyclonal antibodies, monoclonal antibodies, fragments thereof such as F(ab')2, and Fab fragments, as well as any recombinantly produced binding partners. Antibodies are defined to be specifically binding if they bind polypeptides of the invention with a $K_a$ of greater than or equal to about $10^7 M^{-1}$. Affinities of binding partners or antibodies can be readily determined using conventional techniques, for example those described by Scatchard et al., *Ann. N.Y Acad. Sci.*, 51:660 (1949).

Polyclonal antibodies can be readily generated from a variety of sources, for example, horses, cows, goats, sheep, dogs, chickens, rabbits, mice, or rats, using procedures that are well-known in the art. In general, purified polypeptides of the invention, or a peptide based on the amino acid sequence of polypeptides of the invention that is appropriately conjugated, is administered to the host animal typically through parenteral injection. The immunogenicity of these polypeptides can be enhanced through the use of an adjuvant, for example, Freund's complete or incomplete adjuvant. Following booster immunizations, small samples of serum are collected and tested for reactivity to the polypeptides. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530.

Monoclonal antibodies can be readily prepared using well-known procedures, see for example, the procedures described in U.S. Pat. Nos. RE 32,011, 4,902,614, 4,543,439, and 4,411,993; Monoclonal Antibodies, Hybridomas: *A New Dimension in Biological Analyses*, Plenum Press, Kennett, McKearn, and Bechtol (eds.), 1980. Briefly, the host animals, such as Balb/c mice are injected intraperitoneally at least once, and preferably at least twice at about 3 week intervals with isolated and purified polypeptides or conjugated polypeptides of the invention, optionally in the presence of adjuvant. 10 µg of isolated and purified polypeptide of the invention or peptides based on the amino acid sequence of polypeptides of the invention in the presence of RIBI adjuvant (RIBI Corp., Hamilton, Mont.). Mouse sera are then assayed by conventional dot blot technique or antibody capture (ABC) to determine which animal produces the highest level of antibody and whose spleen cells are the best candidate for fusion. Approximately two to three weeks later, the mice are given an intravenous boost of the polypeptides or conjugated polypeptides such as 3 µg suspended in sterile PBS. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG) or more preferably, 50% PEG: 10% DMSO (Sigma). Fusion is plated out into, for example, twenty 96-well flat bottom plates (Corning) containing an appropriate medium, such as HAT supplemented DMEM media and allowed to grow for eight days. Supernatants from resultant hybridomas are collected and added to, for example, a 96-well plate for 60 minutes that is first coated with goat anti-mouse Ig. Following washes, $^{125}$I-polypeptide or peptides of the invention are added to each well, incubated for 60 minutes at room temperature, and washed four times. Positive wells can be subsequently detected by conventional methods, such as autoradiography at −70EC using Kodak X-Omat S film. Positive clones can be grown in bulk culture and supernatants are subsequently purified, such as over a Protein A column (Pharmacia). It is understood of course that many techniques could be used to generate antibodies against polypeptides and fragmented peptides of the invention and that this embodiment in no way limits the scope of the invention.

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Other types of "antibodies" can be produced using the information provided herein in conjunction with the state of knowledge in the art. For example, antibodies that have been engineered to contain elements of human antibodies that are capable of specifically binding polypeptides of the invention are also encompassed by the invention.

Once isolated and purified, the antibodies against polypeptides of the invention can be used to detect the presence of the polypeptides in a sample using established assay protocols. Further, the antibodies of the invention can be used therapeutically or for research purposes to bind to the polypeptides and inhibit its activity in vivo or in vitro.

Antibodies immunoreactive with polypeptides of the invention, and in particular, monoclonal antibodies against these polypeptides, are now made available through the invention. Such antibodies can be useful for inhibiting polypeptide activity in vivo and for detecting the presence of polypeptides of the invention in a sample.

In another embodiment, antibodies generated against a polypeptide and fragmented peptides of the invention can be used in combination with polypeptide or fragmented peptide molecular weight markers of the invention to enhance the accuracy in the use of these molecular weight markers to determine the apparent molecular weight and isoelectric point of a sample protein. Polypeptide or fragmented peptide molecular weight markers of the invention can be mixed with a molar excess of a sample protein and the mixture can be resolved by two dimensional electrophoresis by conventional means. Polypeptides can be transferred to a suitable protein binding membrane, such as nitrocellulose, by conventional means and detected by the antibodies of the invention.

Drug Discovery

The purified polypeptides according to the invention will facilitate the discovery of inhibitors of such polypeptides. The use of a purified polypeptide of the invention in the screening of potential inhibitors thereof is important and can eliminate or reduce the possibility of interfering reactions with contaminants.

In addition, polypeptides of the invention can be used for structure-based design of polypeptide-inhibitors. Such structure-based design is also known as "rational drug design." The polypeptides can be three-dimensionally analyzed by, for example, X-ray crystallography, nuclear magnetic resonance or homology modeling, all of which are well-known methods. The use of the polypeptide structural information in molecular modeling software systems to assist in inhibitor design and inhibitor-polypeptide interaction is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of polypeptides of the invention for likely binding sites of substrates, synthesizing a new molecule that incorporates a predictive reactive site, and assaying the new molecule as described above.

The following examples are presented to promote a fuller understanding of this invention. These examples do not, however, limit the scope of the invention.

EXAMPLE I

Isolation and Identification of a New Human IL-1 Ligand

We screened a human genomic phage library (Stratagene catalog #946205) using a mixture of $^{32}$P-labeled single-strand DNA probes corresponding to the entire coding sequence of murine IL-1 epsilon. After low stringency washing (low stringency washing is defined as 0.2× SSC/0.1% SDS, at room temperature, Ausubel et al. *Current Protocols in Molecular Biology*, Vol. 2, p. 10.3, John Wiley & Sons, Inc., (1996)), a positive clone with a strong hybridization signal was identified. DNA made from this clone and subjected to Southern analysis identified a 5.5 kb Sal I-Asp 718 restriction fragment which was subcloned into pBluescript and sequenced. Homology analysis of the 5.5 kb fragment using the UWGCG computer program "bestfit" revealed that a 212 bp region within the clone was 74% similar at the nucleotide level to the 3 prime exon of murine IL-1 epsilon. As set forth in FIG. 3, this 212 bp sequence contains an open reading frame of 70 amino acids with 66% similarity (64% identity) to the 3 prime exon of murine IL-1 epsilon.

The genomic sequence around the human IL-1 epsilon locus was extended another 5 kb in the 5' direction using a Genome Walking kit (available from Clonetech) in accordance with manufacturer's instructions. Analysis of the sequence of this upstream region revealed three additional putative exons. RT-PCR was used to confirm the expression of these exons, and their linkage into a single IL-1 epsilon cDNA, in RNA from four different human tissue sources (thymus, tonsil, and the cell lines HL-60 and THP-1). Additionally, a cDNA clone was obtained from the Stratagene Universal Human cDNA Library Array I that also demonstrated the joining of the three 3'-most exons. The cDNA clone from the Universal Human cDNA Library Arry I was a partial clone that did not extend to the 5' end of the open reading frame. Full-length human IL-1 epsilon DNA sequences are disclosed in SEQ ID NO:7 and SEQ ID NO:12. The polypeptides encoded by SEQ ID NO:7 and SEQ ID NO:12 are disclosed in SEQ ID NO:8 and SEQ ID NO: 13, respectively. As set forth in FIG. 4, amino acids 51-159 of SEQ ID NO:8 and SEQ ID NO:13 share 53% similarity (49% identity) with the murine IL-1 epsilon (long form).

EXAMPLE II

Chromosome Mapping of Human IL-1 Epsilon by Radiation Hybrid Mapping

PCR was performed using the Whitehead Institute/MIT Center for Genome Research Genebridge4 panel of 93 radiation hybrids (http://www-genome.wi.mit.eduu/ftp/distribution/human_STS_releases/july97/rhmap/genebridge4.html). Primers were used which lie within the putative 3 prime exon of human IL-1 epsilon and which amplify a 195 bp product from human genomic DNA, but do not amplify hamster genomic DNA. The results of the PCRs were converted into a data vector that was submitted to the Whitehead/MIT Radiation Mapping site on the internet (http://www-seq.wi.mit.edu). The data was scored and the chromosomal assignment and placement relative to known Sequence Tag Site (STS) markers on the radiation hybrid map was provided. According to the results, human IL-1 epsilon lies on chromosome 2, at 11.54 cR from STS D2S121 and 4.3 cR from the marker CHLC.GAAT11C03. The following web site provides additional information about radiation hybrid mapping: http://www-genome.wi.mit.edu/ftp/distribution/human_STS_releases/july97/07-97.INTRO.html).

EXAMPLE III

Activation of Signaling Molecules in Human Cells by Human IL-1 Epsilon

The following describes tests and results that were carried out to determine whether 1'-1 epsilon is capable of activating some of the same signaling molecules involved in stress responses as are activated by IL-1α, IL-1β and other inflammatory cytokines.

Human IL-1 epsilon was transfected into COS-1 cells. Several days after the transfection, conditioned medium (containing the transiently expressed IL-1 epsilon) was harvested. Test cells were incubated with this conditioned medium, or alternatively with conditioned medium from COS-1 cells transfected with the empty expression vector. Approximately 10 minutes following the incubation, cell extracts were prepared from the test cells, and the presence of activated signaling molecules was assayed by the use of antibodies specific for the phosphorylated forms of IKBα (phosphorylation on Ser32), p38 MAP kinase (phosphorylation on Thr180 and Tyr182), and Stress-Activated Protein Kinase (SAPK/JNK) (phosphorylation on Thr183/Tyr185) (the antibodies were obtained from New England Biolabs, Beverly, Mass.). These signal transduction molecules are known to be involved in a wide range of cellular responses to stimuli such as UV irradiation, endotoxin, and inflammatory cytokines including IL-1β. Compared to control conditioned medium, conditioned medium containing human II-1 epsilon activated IKBα and p38 MAP kinase phosphorylation in a number of human cell lines including Human Foreskin Fibroblasts and Human Umbelical Vein Endothelial Cells (ATCC CRL-1730). In the non-Hodgkins lymphoma cell line K299, human IL-1 epsilon specifically activated JNK/SAPK phosphorylation. These results demonstrate that IL-1 epsilon is involved in stress response signaling pathways.

EXAMPLE IV

Tissue Distribution of Human IL-1 Epsilon

The tissue distribution of human IL-1 epsilon mRNA was investigated using PCR amplification from a panel of first strand cDNA templates. Specifically, a Clontech (Palo Alto, Calif.) Human Multiple Tissue cDNA Panel was screened using a forward primer in exon 2 and a reverse primer in exon 4, which, together, amplify a 450 base-pair fragment of IL-1 epsilon. The PCR reaction was run for 35 cycles with an annealing temperature of 60EC. PCR products were detected on an agarose gel using ethidium bromide.

Human IL-1 epsilon mRNA was detected in the spleen, lymph node, thymus, tonsil, and leukocyte tissues. The tissue with the highest levels of human IL-1 epsilon mRNA is tonsil.

EXAMPLE V

Activation of ICAM-1 Levels in Human Cells by Human IL-1 Epsilon

The following describes tests and results that were carried out to determine whether Il-1 epsilon is capable of activating some of the same cell surface molecules involved in stress responses as are activated by IL-1α, IL-1β and other inflammatory cytokines.

Human IL-1 epsilon was transfected into COS-1 cells. Several days after the transfection, conditioned medium (containing the transiently expressed IL-1 epsilon) was harvested. Human foreskin fibroblast (HFF) cells were incubated for 18 hours at 37EC with this conditioned medium diluted 1:1 with fresh 0.5% serum-containing medium, or alternatively with conditioned medium from control COS-1 cells transfected with the empty expression vector, diluted 1:1 with fresh 0.5% serum-containing medium.

Following treatment with the conditioned medium from COS-1 cells, the HFF cells were washed twice with PBS and removed from the tissue culture vessel with versene (non-trypsin reagent). Cell-surface ICAM-1 levels were measured by staining with anti-CD54-PE antibody (Pharmingen, San Diego, Calif.) on ice for one hour followed by washing and FACS-based detection.

HFF cells incubated in conditioned medium from control COS-1 cells exhibited a slight increase in ICAM-1 levels, relative to untreated cells. On the other hand, HFF cells that were treated with conditioned medium from COS-1 cells that had been transfected with IL-1 epsilon exhibited a two-fold increase in cell-surface ICAM-1 levels. The level of ICAM-1 staining seen on the IL-1 epsilon treated HFF cells was comparable to that induced on the same cells by purified IL-13.

The specification is most thoroughly understood in light of the teachings of the references cited within the specification, which are hereby incorporated by reference. The embodiments within the specification provide an illustration of embodiments of the invention and should not be construed to limit the scope of the invention. The skilled artisan recognizes many other embodiments are encompassed by the claimed invention.

What is claimed is:

1. An isolated antibody that binds to the polypeptide
   (a) of SEQ ID NO:8.
2. The antibody of claim 1 which is selected from the group consisting of:
   (a) a polyclonal antibody;
   (b) a monoclonal antibody;
   (c) a recombinantly produced antibody; and
   (d) a fragment of the antibodies of (a)-(c) that binds to the polypeptide of SEQ ID NO: 8.
3. The antibody of claim 2, which is isolated and purified.
4. The antibody of claim 3, which inhibits the polypeptide activity.
5. The antibody of claim 1, which is isolated and purified.
6. The antibody of claim 5, which inhibits the polypeptide activity.
7. A monoclonal antibody or fragment thereof that binds to the polypeptide of SEQ ID NO:8.
8. The antibody of claim 7, which is recombinantly produced.
9. The antibody of claim 8, which is isolated and purified.
10. The antibody of claim 9, which inhibits the polypeptide activity.
11. The antibody of claim 7, which is isolated and purified.
12. The antibody of claim 11, which inhibits the polypeptide activity.

* * * * *